(12) United States Patent
Moriya et al.

(10) Patent No.: US 6,331,419 B1
(45) Date of Patent: Dec. 18, 2001

(54) L-GLUTAMIC ACID-PRODUCING BACTERIUM AND METHOD FOR PRODUCING L-GLUTAMIC ACID

(75) Inventors: Mika Moriya; Hiroshi Izui; Eiji Ono; Kazuhiko Matsui; Hisao Ito; Yoshihiko Hara, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/271,438

(22) Filed: Mar. 18, 1999

(30) Foreign Application Priority Data

Mar. 18, 1998 (JP) .................................................. 10-069068
Oct. 19, 1998 (JP) .................................................. 10-297129

(51) Int. Cl.$^7$ ............................... C12N 1/00; C12N 1/20; C12P 1/04; C12P 13/04; C12P 13/14
(52) U.S. Cl. .......................... 435/110; 435/106; 435/170; 435/252.1; 435/822; 435/880
(58) Field of Search ................................. 435/252.1, 822, 435/106, 880, 110, 170

(56) References Cited

U.S. PATENT DOCUMENTS 3,563,857 * 2/1971 Oki et al. .............................. 195/49
5,643,769 * 7/1997 Katsumata et al. .................. 435/106

FOREIGN PATENT DOCUMENTS

| 0 670 370 | 9/1995 | (EP) . |
| 7-203980 (6-825) | 8/1995 | (JP) . |

* cited by examiner

Primary Examiner—Deborah K. Ware
(74) Attorney, Agent, or Firm—Oblon, Spivak, McClelland, Maier & Neustadt, P.C.

(57) ABSTRACT

L-Glutamic acid is produced by culturing in a liquid culture medium a microorganism belonging to the genus Enterobacter or Serratia. Further, the microorganism having an ability to produce L-glutamic acid, which increases in an activity of enzyme catalyzing a reaction for L-glutamic acid biosynthesis, or which decreases in or is deficient in an activity of an enzyme catalyzing a reaction branching from a pathway for L-glutamic acid biosynthesis and producing a compound other than L-glutamic acid, and collecting produced L-glutamic acid from the culture medium.

12 Claims, 10 Drawing Sheets

```
  1'  MQNSAMKPWLDSSWLAGANQSYIEQLYEDFLTDPDSVDAVWRSMFQQLPGTGVKPEQFHS
      ***** * ***** * ***** ******************* *** *********** ****

1'  MQNSALKAWLDSSYLSGANQSWIEQLYEDFLTDPDSVDANWRSTFQQLPGTGVKPDQFHS

61'  ATREYFRRLAKDASRYTSSVTDPATNSKQVKVLQLINAFRFRGHQEANLDPLGLWKQDRV
      *************** *  ** ** *********** ****** ********* ** *

61'  QTREYFRRLAKDASRYSSTISDPDTNVKQVKVLQLINAYRFRGHQHANLDPLGLWQQDKV

121'  ADLDPAFHDLTDADFQESFNVGSFAIGKETMKLADLFDALKQTYCGSIGAEYMHINNTEE
      ***** ***** ******* ******* * ******** ******** ***

121'  ADLDPSFHDLTEADFQETFNVGSFASGKETMKLGELLEALKQTYCGPIGAEYMHITSTEE

181'  KRWIQQRIESGASQTSFSGEEKKGFLKELTAAEGLEKYLGAKFPGAKRFSLEGGDALVPM
      ***********    *   **** ** ********* ******************** **

181'  KRWIQQRIESG--RATFNSEEKKRFLSELTAAEGLERYLGAKFPGAKRFSLEGGDALIPM

241'  LREMIRHAGKSGTREVVLGMAHRGRLNVLINVLGKKPQDLFDEFSGKHKEHLGTGDVKYH
      * ******* ************************ *************** *************

239'  LKEMIRHAGNSGTREVVLGMAHRGRLNVLVNVLGKKPQDLFDEFAGKHKEHLGTGDVKYH

301'  MGFSSDIETEGGLVHLALAFNPSHLEIVSPVVMGSVRARLDRLAEPVSNKVLPITIHGDA
      ****** * ************************** ********* ** *************

299'  MGFSSDFQTDGGLVHLALAFNPSHLEIVSPVVIGSVRARLDRLDEPSSNKVLPITIHGDA

361'  AVIGQGVVQETLNMSQARGYEVGGTVRIVINNQVGFTTSNPKDARSTPYCTDIGKMVLAP
      ** *********************************** **************** **

359'  AVTGQGVVQETLNMSKARGYEVGGTVRIVINNQVGFTTSNPLDARSTPYCTDIGKMVQAP

421'  IFHVNADDPEAVAFVTRLALDYRNTFKRDVFIDLVCYRRHGHNEADEPSATQPLMYQKIK
      ******************** ************ ************ ************************

419'  IFHVNADDPEAVAFVTRLALDFRNTFKRDVFIDLVSYRRHGHNEADEPSATQPLMYQKIK
```

*FIG. 7A*

```
481'  KHPTPRKIYADRLEGEGVASQEDATEMVNLYRDALDAGECVVPEWRPMSLHSFTWSPYLN
      ********** ** * **  ***************** *** *****  **********

479'  KHPTPRKIYADKLEQEKVATLEDATEMVNLYRDALDAGDCVVAEWRPMNMHSFTWSPYLN

541'  HEWDEPYPAQVDMKRLKELALRISQVPEQIEVQSRVAKIYNDRKLMAEGEKAFDWGGAEN
      ***** **  * **** *** *** ***  * ******** **  ** *** ********

539'  HEWDEEYPNKVEMKRLQELAKRISTVPEAVEMQSRVAKIYGDRQAMAAGEKLFDWGGAEN

601'  LAYATLVDEGIPVRLSGEDSGRGTFFHRHAVVHNQANGSTYTPLHHIHNSQGEFKVWDSV
      ****************************** *** ******** **** ** * *****

599'  LAYATLVDEGIPVRLSGEDSGRGTFFHRHAVIHNQSNGSTYTPLQHIHNGQGAFRVWDSV

661'  LSEEAVLAFEYGYATAEPRVLTIWEAQFGDFANGAQVVIDQFISSGEQKWGRMCGLVMLL
      ******************** ***************************************

659'  LSEEAVLAFEYGYATAEPRTLTIWEAQFGDFANGAQVVIDQFISSGEQKWGRMCGLVMLL

721'  PHGYEGQGPEHSSARLERYLQLCAEQNMQVCVPSTPAQVYHMLRRQALRGMRRPLVVMSP
      ************************************************************

719'  PHGYEGQGPEHSSARLERYLQLCAEQNMQVCVPSTPAQVYHMLRRQALRGMRRPLVVMSP

781'  KSLLRHPLAISSLDELANGSFQPAIGEIDDLDPQGVKRVVLCSGKVYYDLLEQRRKDEKT
      ********* *** ***** * ******* *** ****** ****************

779'  KSLLRHPLAVSSLEELANGTFLPAIGEIDELDPKGVKRVVMCSGKVYYDLLEQRRKNNQH

841'  DVAIVRIEQLYPFPHQAVQEALKAYSHVQDFVWCQEEPLNQGAWYCSQHHFRDVVPFGAT
      ************** * ** *    ** ******************** * ****

839'  DVAIVRIEQLYPFPHKAMQEVLQQFAHVKDFVWCQEEPLNQGAWYCSQHHFREVIPFGAS

901'  LRYAGRPASASPAVGYMSVHQQQQQDLVNDALNVN
      ************************* ************

899'  LRYAGRPASASPAVGYMSVHQKQQQDLVNDALNVE
```

*FIG. 7B*

```
  1'  MSSVDILVPDLPESVADATVATWHKKPGDAVSRDEVIVEIETDKVVLEVPASADGVLEAV
      ********************************** **** ****************** * **

1"  MSSVDILVPDLPESVADATVATWHKKPGDAVVRDEVLVEIETDKVVLEVPASADGILDAV

61'  LEDEGATVTSRQILGRLKEGNSAGKESSAKAESNDTTPAQRQTASLEEESSDALSPAIRR
      *****  **********  ********  ***  *     ******  *****   ********

61"  LEDEGTTVTSRQILGRLREGNSAGKETSAKSEEKASTPAQRQQASLEEQNNDALSPAIRR

121'  LIAEHNLDAAQIKGTGVGGRLTREDVEKHLANKPQAEKAAAPAAGAATAQQPVANRSEKR
      * *******   ******************   *   *   **** *   **    *  *****

121"  LLAEHNLDASAIKGTGVGGRLTREDVEKHLAKAPAKE--SAPAAAAPAAQPALAARSEKR

181'  VPMTRLRKRVAERLLEAKNSTAMLTTFNEINMKPIMDLRKQYGDAFEKRHGVRLGFMSFY
      ******************************** ************* ******* *******

179"  VPMTRLRKRVAERLLEAKNSTAMLTTFNEVNMKPIMDLRKQYGEAFEKRHGIRLGFMSFY

241'  IKAVVEALKRYPEVNASIDGEDVVYHNYFDVSIAVSTPRGLVTPVLRDVDALSMADIEKK
       ********************  ************  ******************  *  *******

239"  VKAVVEALKRYPEVNASIDGDDVVYHNYFDVSMAVSTPRGLVTPVLRDVDTLGMADIEKK

301'  IKELAVKGRDGKLTVDDLTGGNFTITNGGVFGSLMSTPIINPPQSAILGMHAIKDRPMAV
      ***************** ******************************************

299"  IKELAVKGRDGKLTVEDLTGGNFTITNGGVFGSLMSTPIINPPQSAILGMHAIKDRPMAV

361'  NGQVVILPMMYLALSYDHRLIDGRESVGYLVAVKEMLEDPARLLLDV
      ****  **********************  **  **  ****  ******

359"  NGQVEILPMMYLALSYDHRLIDGRESVGFLVTIKELLEDPTRLLLDV
```

*FIG. 8*

1'      MNLHEYQAKQLFARYGMPAPTGYACTTPREAEEAASKIGAG
        ************** * ********************

1'      MNLHEYQAKQLFARYGLPAPVGYACTTPREAEEAASKIGAGPWVVKCQVHAGGRGKAGGV

FIG. 9

1'                      AFSVFRCHSIMNCVSVCPKGLNPTRAIGHIKSMLLQRSA
                        ************************************** *

181'    FLIDSRDTETDSRLDGLSDAFSVFRCHSIMNCVSVCPKGLNPTRAIGHIKSMLLQRNA

FIG. 10

L-GLUTAMIC ACID-PRODUCING BACTERIUM AND METHOD FOR PRODUCING L-GLUTAMIC ACID

BACKGROUND OF THE INVENTION

The present invention relates to a novel L-glutamic acid-producing bacterium and a method for producing L-glutamic acid by fermentation using the same. L-Glutamic acid is an important amino acid as food, drugs and the like.

L-Glutamic acid has conventionally been produced by fermentation methods utilizing the so-called coryneform L-glutamic acid-producing bacteria which principally belong to the genera Brevibacterium, Corynebacterium, and Microbacterium or variants thereof ("Amino Acid Fermentation", Gakkai Shuppan Center, pp.195–215, 1986). As methods for producing L-glutamic acid by fermentation utilizing other bacterial strains, there have been known the methods utilizing microorganisms of the genera Bacillus, Streptomyces, Penicillium and the like (U.S. Pat. No. 3,220,929), the methods utilizing microorganisms of the genera Pseudomonas, Arthrobacter, Serratia, Candida and the like (U.S. Pat. No. 3,563,857), the methods utilizing microorganisms of the genera Bacillus, Pseudomonas, Serratia and the like or Aerobacter aerogenes (currently referred to as Enterobacter aerogenes) (Japanese Patent Publication (KOKOKU) No. 32-9393(1957)), the method utilizing variant strains of *Escherichia coli* (Japanese Patent Application Laid-Open (KOKAI) No. 5-244970(1993)) and the like.

Though the productivity of L-glutamic acid has considerably been improved by breeding of such microorganisms as mentioned above or improvements of production methods, it is still desired to develop a more inexpensive and more efficient method for producing L-glutamic acid in order to meet the expected markedly increasing future demand of the amino acid.

SUMMARY OF THE INVENTION

The object of the present invention is to find a novel L-glutamic acid-producing bacterium having a high ability to produce L-glutamic acid, thereby developing a more inexpensive and more efficient method for producing L-glutamic acid.

To achieve the aforementioned object, the present inventors intensively searched for and studied microorganisms having the ability to produce L-glutamic acid that are different from the previously reported microorganisms. As a result, they found that certain strains derived from microorganisms belonging to the genus Enterobacter or Serratia had a high ability to produce L-glutamic acid, and have completed the present invention.

Thus, the present invention provide:

(1) a microorganism belonging to the genus Enterobacter or Serratia and having an ability to produce L-glutamic acid and at least one of the following properties:
  (a) the microorganism increases in an activity of an enzyme catalyzing a reaction for L-glutamic acid biosynthesis; and
  (b) the microorganism decreases in or is deficient in an activity of an enzyme catalyzing a reaction branching from a pathway for L-glutamic acid biosynthesis and producing a compound other than L-glutamic acid;

(2) a microorganism of the above (1) wherein the enzyme catalyzing the reaction for the L-glutamic acid biosynthesis is at least one selected from the group consisting of citrate synthase (abbreviated as "CS" hereinafter), phosphoenolpyruvate carboxylase (abbreviated as "PEPC" hereinafter), and glutamate dehydrogenase (abbreviated as "GDH" hereinafter);

(3) a microorganism of the above (2) wherein the enzyme catalyzing the reaction for the L-glutamic acid biosynthesis includes all of CS, PEPC and GDH;

(4) a microorganism of any one of the above (1) to (3) wherein the enzyme catalyzing the reaction branching from the pathway for L-glutamic acid biosynthesis and producing the compound other than L-glutamic acid is α-ketoglutarate dehydrogenase (abbreviated as "αKGDH" hereinafter);

(5) a microorganism of any one of the above (1) to (4) which is *Enterobacter agglomerans* or *Serratia liquefacience;* and (6) a method for producing L-glutamic acid which comprises culturing the microorganism as defined in any one of the above (1) to (5) in a liquid culture medium to produce and accumulate L-glutamic acid in the culture medium, and collecting the L-glutamic acid from the culture medium.

Because the microorganism of the present invention have a high ability to produce L-glutamic acid, it is considered to be possible to impart a further higher production ability to the microorganism by using the breeding techniques previously known for the coryneform L-glutamic acid-producing bacteria and the like, and it is expected to contribute to development of a more inexpensive and more efficient method for producing L-glutamic acid by appropriately selecting culture conditions and the like.

BRIEF EXPLANATION OF THE DRAWINGS

FIG. 7 shows comparison of an amino acid sequence deduced from a nucleotide sequence of a sucA gene derived from *Enterobacter agglomerans* (SEQ ID NO: 8) with one derived from *Escherichia coli* (SEQ ID NO: 9). The upper sections: *Enterobacter agglomerans,* the lower sections: *Escherichia coil* (the same shall apply hereinafter).

FIG. 8 shows comparison of an amino acid sequence deduced from a nucleotide sequence of a sucB gene derived from *Enterobacter agglomerans* (SEQ ID NO: 10) with one derived from *Escherichia coli* (SEQ ID NO:11).

FIG. 9 shows comparison of an amino acid sequence deduced from a nucleotide sequence of a sdhB gene derived from *Enterobacter agglomerans* (SEQ ID NO: 12) with one derived from *Escherichia coli* (SEQ ID NO: 13).

FIG. 10 shows comparison of an amino acid sequence deduced from a nucleotide sequence of a sucC gene derived from *Enterobacter agglomerans* (SEQ ID NO: 14) with one derived from *Escherichia coli* (SEQ ID NO: 15).

DETAILED DESCRIPTION OF THE INVENTION

Figure 1:
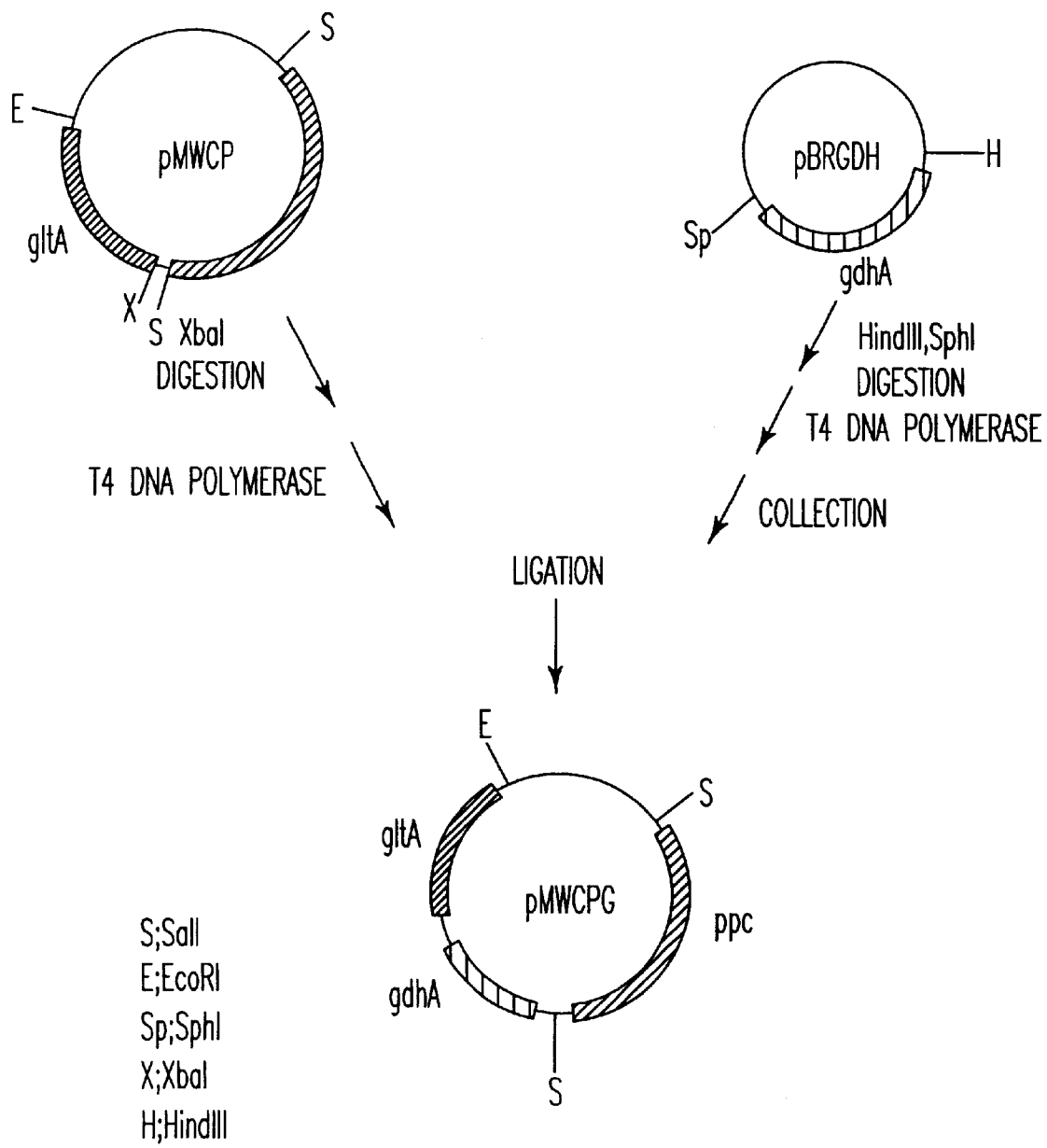
FIG. 1 shows construction of a plasmid pMWCPG having a gltA gene, a ppc gene and a gdha gene.

The present invention will be explained in detail hereinafter.

The microorganism of the present invention is a microorganism belonging to the genus Enterobacter or Serratia, and having at least one of the following properties:

(a) the microorganism increases in an activity of an enzyme catalyzing a reaction for L-glutamic acid biosynthesis; and (b) the microorganism decreases in or is deficient in an activity of an enzyme catalyzing a reaction branching from a pathway for L-glutamic acid biosynthesis and producing a compound other than L-glutamic acid.

Such a microorganism can be obtained by using a microorganism belonging to the genus Enterobacter or the genus Serratia as a parent strain, and imparting the properties of the above (a) and/or (b) to the microorganism. Examples of the microorganism belonging to the genus Enterobacter or the genus Serratia that can be used as the parent strain are listed below:

*Enterobacter agglomerans*
*Enterobacter aerogenes*
*Enterobacter amnigenus*
*Enterobacter asburiae*
*Enterobacter cloacae*
*Enterobacter dissolvens*
*Enterobacter gergoviae*
*Enterobacter hormaechei*
*Enterobacter intermedius*
*Enterobacter nimipressuralis*
*Enterobacter sakazakii*
*Enterobacter taylorae*
*Serratia liquefacience*
*Serratia entomophila*
*Serratia ficaria*
*Serratia fonticola*
*Serratia grimesii*
*Serratia proteamaculans*
*Serratia odorifera*
*Serratia plymuthica*
*Serratia rubidaea*

More preferably, those bacterial strains listed below can be mentioned:

*Enterobacter agglomerans* ATCC 12287
*Enterobacter agglomerans* AJ13355
*Serratia liquefacience* ATCC 14460

The *Enterobacter agglomerans* AJ13355 was deposited at the National Institute of Bioscience and Human-Technology, Agency of Industrial Science and Technology, Ministry of International Trade and Industry on Feb. 19, 1998, and received an accession number of FERM P-16644, and then transferred to an international deposition under the Budapest Treaty on Jan. 11, 1999, and received an accession number of FERM BP-6614. The *Enterobacter agglomerans* ATCC 12287, and the *Serratia liquefacience* ATCC 14460 are available from ATCC.

The *Enterobacter agglomerans* AJ13355 is a strain solated from soil in Iwata-shi, Shizuoka, Japan.

Physiological properties of AJ13355 are as follows:

(1) Gram stain: Negative
(2) Behavior for oxygen: Facultative anaerobe
(3) Catalase: Negative
(4) Oxidase: Positive
(5) Nitrate reduction: Negative
(6) Voges-Proskauer reaction: Positive
(7) Methyl Red test: Negative
(8) Urease: Negative
(9) Indole production: Positive
(10) Motility: Present
(11) Hydrogen sulfide production in TSI culture medium: Slightly active
(12) β-Galactosidase: Positive
(13) Sugar assimilability:
  Arabinose: Positive
  Sucrose: Positive
  Lactose: Positive
  Xylose: Positive
  Sorbitol: Positive
  Inositol: Positive
  Trehalose: Positive
  Maltose: Positive
  Melibiose: Positive
  Adonitol: Negative
  Raffinose: Positive
  Salicin: Negative
  Melibiose: Positive:
(14) Glycerose assimilability: Positive
(15) Organic acid assimilability:
  Citric acid: Positive
  Tartaric acid: Negative
  Gluconic acid: Positive
  Acetic acid: Positive
  Malonic acid: Negative
(16) Arginine dehydratase: Negative
(17) Ornithine decarboxylase: Negative
(18) Lysine decarboxylase: Negative
(19) Phenylalanine deaminase: Negative
(20) Pigment formation: Yellow
(21) Gelatin liquefaction: Positive
(22) Growth pH: Not good growth at pH 4, good growth at pH 4.5 to 7
(23) Growth temperature: Good growth at 25° C., good growth at 30° C., good growth at 37° C., growth possible at 42° C., no growth at 45° C.

From these bacteriological properties, AJ13355 is determined to be *Enterobacter agglomerans*.

In the working examples described hereinafter, *Enterobacter agglomerans* ATCC12287, *Enterobacter agglomerans* AJ13355, and *Serratia liquefacience* ATCC14460 were used as starting parent strains for obtaining strains which increase in the activity of the enzyme catalyzing the reactions for the L-glutamic acid biosynthesis, or strains which decrease in or are deficient in the activity of the enzyme catalyzing the reaction branching from the pathway for L-glutamic acid biosynthesis and producing the compound other than L-glutamic acid. However, the sugar metabolism by any of bacteria belonging to the genera Enterobacter and Serratia is achieved via the Embden-Meyerhof pathway, and pyruvate produced in the pathway is oxidized in the tricarboxylic acid cycle under aerobic conditions. L-Glutamic acid is biosynthesized from (α-ketoglutaric acid which is an intermediate of the tricarboxylic acid cycle by GDH or glutamine synthetase/glutamate synthase. Thus, these microorganisms share the same biosynthetic pathway for L-glutamic acid, and microorganism belonging to the genera Enterobacter and Serratia are encompassed within a single concept according to the present invention. Therefore, microorganisms belonging to the genera Enterobacter and Serratia other than species and strains specifically mentioned above also fall within the scope of the present invention.

The microorganism of the present invention is a microorganism belonging to the genus Enterobacter or the genus Serratia and having an ability to produce L-glutamic acid. The expression "having an ability to produce L-glutamic acid" as herein used means to have an ability to accumulate L-glutamic acid in a culture medium during cultivation. According to the present invention, the ability to produce L-glutamic acid is imparted by giving either one or both of the following characteristics:

(a) the microorganism increases in the activity of the enzyme catalyzing the reaction for the L-glutamic acid biosynthesis; and (b) the microorganism decreases in or is deficient in the activity of the enzyme catalyzing the reaction 2)branching from the pathway for L-glutamic acid biosynthesis and producing the compound other than L-glutamic acid.

As examples of the enzyme catalyzing the reaction for L-glutamic acid biosynthesis of microorganisms of the genus Enterobacter or Serratia, there can be mentioned GDH, glutamine synthetase, glutamate synthase, isocitrate dehydrogenase, aconitate hydratase, CS, PEPC, pyruvate dehydrogenase, pyruvate kinase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase and the like. Among these enzymes, one or two or three kinds of CS, PEPC and GDH are preferred. As for the microorganism of the present invention, it is further preferred that activities of all of the three kinds of enzymes, CS, PEPC and GDH, are increased. Whether a microorganism increases in an activity of a target enzyme, and degree of the increase of the activity can be determined by measuring the enzyme activity of a bacterial cell extract or a purified fraction, and comparing it with that of a wild type strain or a parent strain.

The microorganism of the present invention, which belongs to the genus Enterobacter or Serratia, and increases in the activity of the enzyme catalyzing the reaction for L-glutamic acid biosynthesis, can be obtained as, for example, a variant where mutation has been made in a gene encoding the enzyme or a genetic recombinant strain by using any of the microorganisms mentioned above as a starting parent strain.

To enhance the activity of CS, PEPC or GDH, for example, a gene encoding CS, PEPC or GDH can be cloned in a suitable plasmid, and the aforementioned starting parent strain as a host can be transformed with the resulting plasmid. This can increase the copy number of each of the genes encoding CS, PEPC and GDH (hereinafter abbreviated as "gltA gene", "ppc gene", and "gdhA gene", respectively), and as a result the activities of CS, PEPC and GDH can be increased.

One or two or three kinds selected from the cloned gltA gene, ppc gene and gdhA gene in any combination are introduced into the starting parent strain mentioned above. When two or three kinds of the genes are introduced, either the two or three kinds of the genes are cloned in one kind of plasmid, and introduced into the host, or they are separately cloned in two or three kinds of plasmids that can exist in the same host, and introduced into the host.

The plasmid is not particularly limited so long as it can autonomously replicate in a microorganism belonging to the genus Enterobacter or Serratia. Examples of the plasmid include, for example, pUC19, pUC18, pBR322, pHSG299, pHSG298, pHSG399, pHSG398, RSF1010, pMW119, pMW118, pMW219, pMW218 and the like. Other than these plasmids, phage DNA vectors can also be utilized.

Transformation can be achieved by, for example, the method of D. M. Morrison (Methods in Enzymology 68, 326 (1979)), the method by increasing permeability of recipient cells for DNA with calcium chloride (Mandel, M. and Higa, A., J. Mol. Biol., 53, 159 (1970)), or the like.

The activities of CS, PEPC and GDH can also be increased by using multiple copies of the gltA gene, the ppc gene and/or the gdh gene present on the chromosome DNA of the starting parent strain as a host. In order to introduce multiple copies of the gltA gene, the ppc gene and/or the gdhA gene into a chromosome DNA of a microorganism belonging to the genus Enterobacter or Serratia, sequences present on chromosome DNA in a multiple copy number such as repetitive DNA, and inverted repeats present at an end of transposition factors can be utilized. Alternatively, multiple copies of the genes can also be introduced into a chromosome DNA by utilizing transposition of transposons carrying the gltA gene, the ppc gene, or the gdhA gene. These techniques can increase the copy number of the gltA gene, the ppc gene, and the gdhA gene in transformant cells, and as a result increase the activities of CS, PEPC and GDH.

Any organisms can be used as a source of the gltA gene, the ppc gene and the gdhA gene used for increasing copy numbers, so long as the organisms have the CS, PEPC and GDH activities. Among such organisms, bacteria, i.e., prokaryotes, such as those bacteria belonging to the genera Enterobacter, Klebsiella, Erwinia, Pantoea, Serratia, Escherichia, Corynebacterium, Brevibacterium, and Bacillus are preferred. As a specific example, *Escherichia coli* can be mentioned. The gltA gene, the ppc gene and the gdhA gene can be obtained from a chromosome DNA of such microorganisms as mentioned above.

The gltA gene, the ppc gene and the gdhA gene can each be obtained from a chromosome DNA of any of the aforementioned microorganisms by isolating a DNA fragment complementing auxotrophy of a variant strain lacking the CS, PEPC or GDH activity. Alternatively, because the nucleotide sequences of these genes of bacteria of the genus Escherichia or Corynebacterium have already been elucidated (Biochemistry, Vol. 22, pp.5243–5249, 1983; J. Biochem. Vol. 95, pp.909–916, 1984; Gene, Vol. 27, pp.193–199, 1984; Microbiology, Vol. 140, pp.1817–1828, 1994; Mol. Gen. Genet. Vol. 218, pp.330–339, 1989; and Molecular Microbiology, Vol. 6, pp.317–326, 1992), the genes can be obtained by PCR using primers synthesized based on each of the elucidated nucleotide sequences, and the chromosome DNA as a template.

The activity of CS, PEPC or GDH can also be increased by, other than by the gene amplification mentioned above, enhancing expression of the gltA gene, the ppc gene or the gdhA gene. For example, the expression is enhanced by replacing the promoter of the gltA gene, the ppc gene, or the gdhA gene with another stronger promoter. Examples of such a strong promoter include, for example, a lac promoter, a trp promoter, a trc promoter, a tac promoter, a $P_R$ promoter and a $P_L$ promoter of lambda phage and the like. The gltA gene, the ppc gene, or the gdhA gene of which promoter has been substituted is cloned into a plasmid and introduced into a host microorganism, or introduced into a chromosome DNA of host microorganism using a repetitive DNA, inverted repeat, transposon or the like.

The activities of CS, PEPC or GDH can also be increased by replacing the promoter of the gltA gene, the ppc gene, or the gdhA gene on a chromosome with another stronger promoter (see WO87/03006, and Japanese Patent Application Laid-Open (KOKAI) No. 61-268183(1986)), or inserting a strong promoter at the upstream of each coding sequence of the genes (see Gene, 29, pp. 231–241, 1984). Specifically, these are achieved by homologous recombination between the gltA gene, the ppc gene, or the gdhA gene of which promoter is replaced with a stronger promoter or DNA containing a part of them, and a corresponding gene on the chromosome.

Specific examples of the microorganism belonging to the genus Enterobacter or Serratia of which CS, PEPC or GDH activity is increased include, for example, *Enterobacter agglomerans* ATCC12287/RSFCPG, *Enterobacter agglomerans* AJ13355/RSFCPG, and *Serratia liquefacience* ATCC14460/RSFCPG.

Examples of the enzyme catalyzing the reaction branching from the pathway of L-glutamic acid biosynthesis and producing the compound other than L-glutamic acid include, for example, αKGDH, isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase and the like. Among these enzymes, αKGDH is preferred.

In order to obtain such decrease or deficiency of enzyme activity as mentioned above in a microorganism belonging to the genus Enterobacter or Serratia, a mutation causing the decrease or deficiency of the enzyme activity can be introduced into a gene encoding the enzyme by a conventional mutagenesis technique or genetic engineering technique.

Examples of the mutagenesis technique include, for example, the method utilizing irradiation of X-ray or ultraviolet light, the method utilizing treatment with a mutagenic agent such as N-methyl-N'-nitro-N-nitrosoguanidine and the like. The site of gene to which a mutation is introduced may be a coding region encoding an enzyme protein, or an expression regulatory region such as a promoter.

Examples of the genetic engineering technique include, for example, genetic recombination, genetic transduction, cell fusion and the like. For example, a drug resistance gene is inserted into a target gene to produce a functionally inactivated gene (defective gene). Then, this defective gene is introduced into a cell of a microorganism belonging to the genus Enterobacter or Serratia, and the target gene on a chromosome is replaced with the defective gene by homologous recombination (gene disruption).

Whether a microorganism decreases in an activity of a target enzyme or is deficient in the activity, and degree of the decrease of the activity can be determined by measuring the enzyme activity of a bacterial cell extract or a purified fraction of a candidate strain, and comparing it with that of a wild type strain or a parent strain. The αKGDH enzymatic activity can be measured by, for example, the method of Reed et al. (L. J. Reed and B. B. Mukherjee, Methods in Enzymology 1969, 13, p.55–61).

Depending on the target enzyme, a target variant can be selected based on a phenotype of the variant. For example, a variant which is deficient in the αKGDH activity or decreases in the activity cannot grow on a minimal medium containing glucose, or a minimal medium containing acetic acid or L-glutamic acid as an exclusive carbon source, or shows markedly reduced growth rate therein under aerobic conditions. However, even under the same condition, it can exhibit normal growth by addition of succinic acid or lysine, methionine and diaminopimelate to the minimal medium containing glucose. Based on these phenomena, a variant that is deficient in the αKGDH activity or decreases in the activity can be selected.

A method for producing a *Brevibacterium lactofermentum* strain lacking the αKGDH gene based on homogenous recombination is detailed in WO95/34672, and a similar method can be used for microorganisms belonging to the genera Enterobacter and Serratia.

In addition, procedures of genetic cloning, cleavage and ligation of DNA, transformation and the like are detailed in Molecular Cloning, 2nd edition, Cold Spring Harbor Press (1989) and the like.

An example of the variant strain that is deficient in the αKGDH activity or decreases in the activity obtained as described above is *Enterobacter agglomerans* AJ13356. The *Enterobacter agglomerans* AJ13356 was deposited at the National Institute of Bioscience and Human-Technology, Agency of Industrial Science and Technology, Ministry of International Trade and Industry on Feb. 19, 1998, received an accession number of FERM P-16645, and then transferred to an international deposition under the Budapest Treaty on Jan. 11, 1999, and received an accession number of FERM BP-6615.

The microorganism belonging to the genus Enterobacter or Serratia, and having at least one of the properties (a) and (b) and an ability to produce L-glutamic acid can be cultured in a liquid medium to produce and accumulate L-glutamic acid in the medium.

The culture medium may be an ordinary nutrient medium containing a carbon source, a nitrogen source, and inorganic salts, as well as organic trace nutrients such as amino acids, vitamins and the like, as required. It can be a synthetic medium or a natural medium. Any carbon sources and nitrogen sources can be used for the culture medium so long as they can be utilized by the microorganism to be cultured.

The carbon source may be a saccharide such as glucose, glycerol, fructose, sucrose, maltose, mannose, galactose, starch hydrolysates, molasses and the like. further, an organic acid such as acetic acid and citric acid may also be used alone or in combination with other carbon sources.

The nitrogen source may be ammonia, ammonium salts such as ammonium sulfate, ammonium carbonate, ammonium chloride, ammonium phosphate, and ammonium acetate, nitrates and the like.

As organic trace nutrients, amino acids, vitamins, fatty acids, nucleic acids, materials containing them such as peptone, casamino acid, yeast extract, and soybean protein decomposition products and the like are used, and when an auxotrophic variant which requires an amino acid or the like for its growth is used, it is necessary to complement the nutrient required.

As the inorganic salt, phosphates, magnesium salts, calcium salts, iron salts, manganese salts and the like are used.

As for the culture conditions, cultivation may be performed under aerobic conditions at a temperature of 20 to 42° C. and a pH of 4 to 8. The cultivation can be continued for 10 hours to 4 days to accumulate a considerable amount of L-glutamic acid in the liquid culture medium.

After the completion of the cultivation, L-glutamic acid accumulated in the culture medium may be collected by a known method. For example, it can be isolated by a method comprising concentrating the medium after removing the cells to crystallize the product, ion exchange chromatography or the like.

EXAMPLES

The present invention will be explained more specifically with reference to the following examples.

(1) Construction of Plasmid Having gltA Gene, ppc Gene and gdhA Gene

Procedure for construction of a plasmid having a gltA gene, a ppc gene and a gdhA gene will be explained by referring to FIG. 1 to FIG. 5.

A plasmid pBRGDH having a gdhA gene derived from *Escherichia coli* (Japanese Patent Application Laid-Open (KOKAI) No. 7-203980(1995)) was digested with HindIII and SphI, and the both ends were blunt-ended by a treatment with T4 DNA polymerase. Then, a DNA fragment containing the gdhA gene was purified and collected. On the other hand, a plasmid pMWCP having a gltA gene and a ppc gene derived from *Escherichia coli* (WO97/08294) was digested with XbaI, and the both ends were blunt-ended by a treatment with T4 DNA polymerase. This was mixed with the DNA fragment having the gdhA gene purified above, and ligated with T4 ligase, giving a plasmid pMWCPG, which corresponds to the pMWCP further carrying the gdhA gene (FIG. 1).

Figure 2:
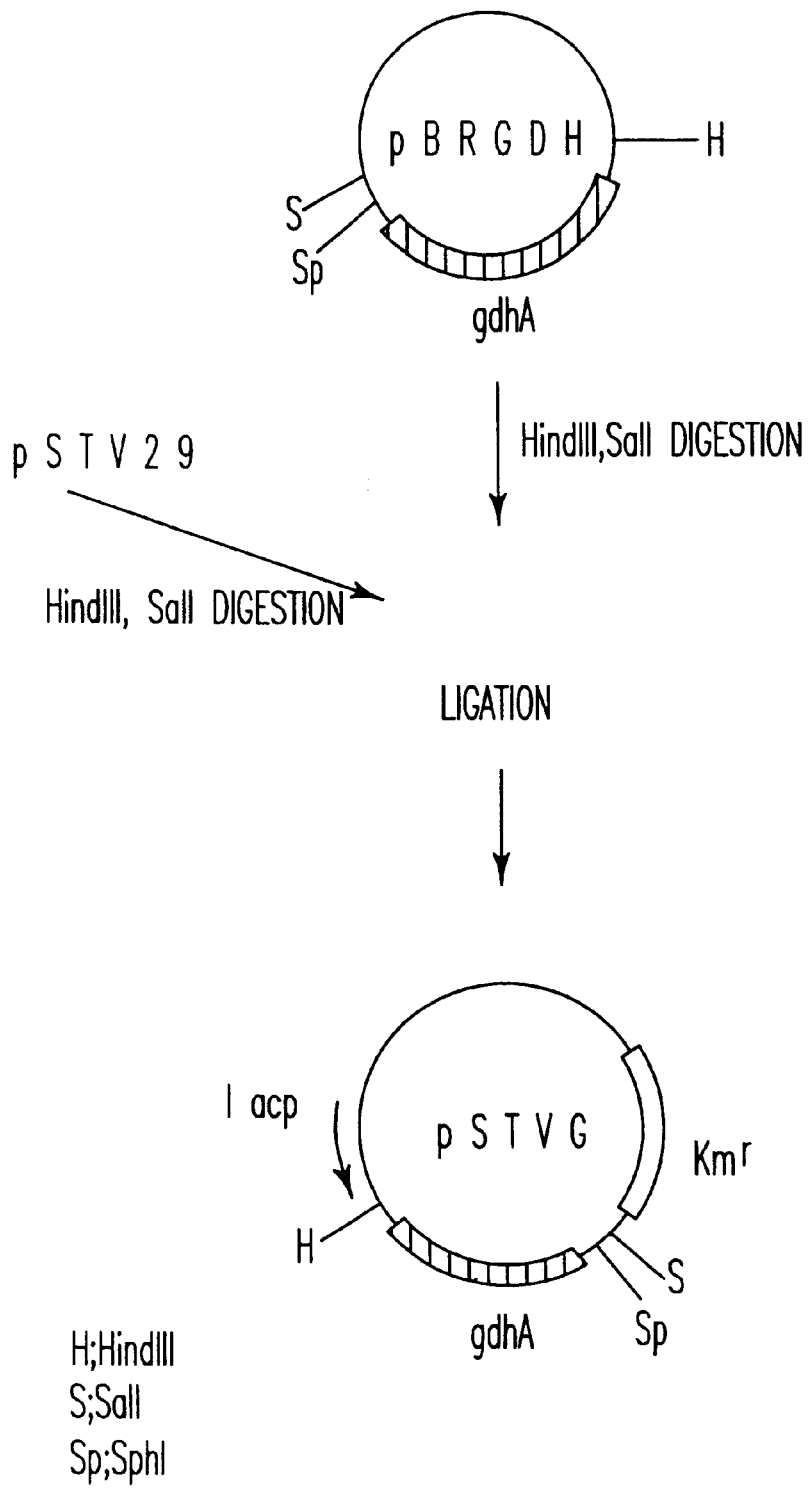
FIG. 2 shows construction of a plasmid pSTVG having the gdhA gene.

A DNA fragment having the gdhA gene obtained by digesting the pBRGDH with HindIII and SalI was purified and collected, and introduced into the HindIII-SalI site of a plasmid pSTV29 (purchased from Takara Shuzo) to obtain a plasmid PSTVG (FIG. 2).

Figure 3:
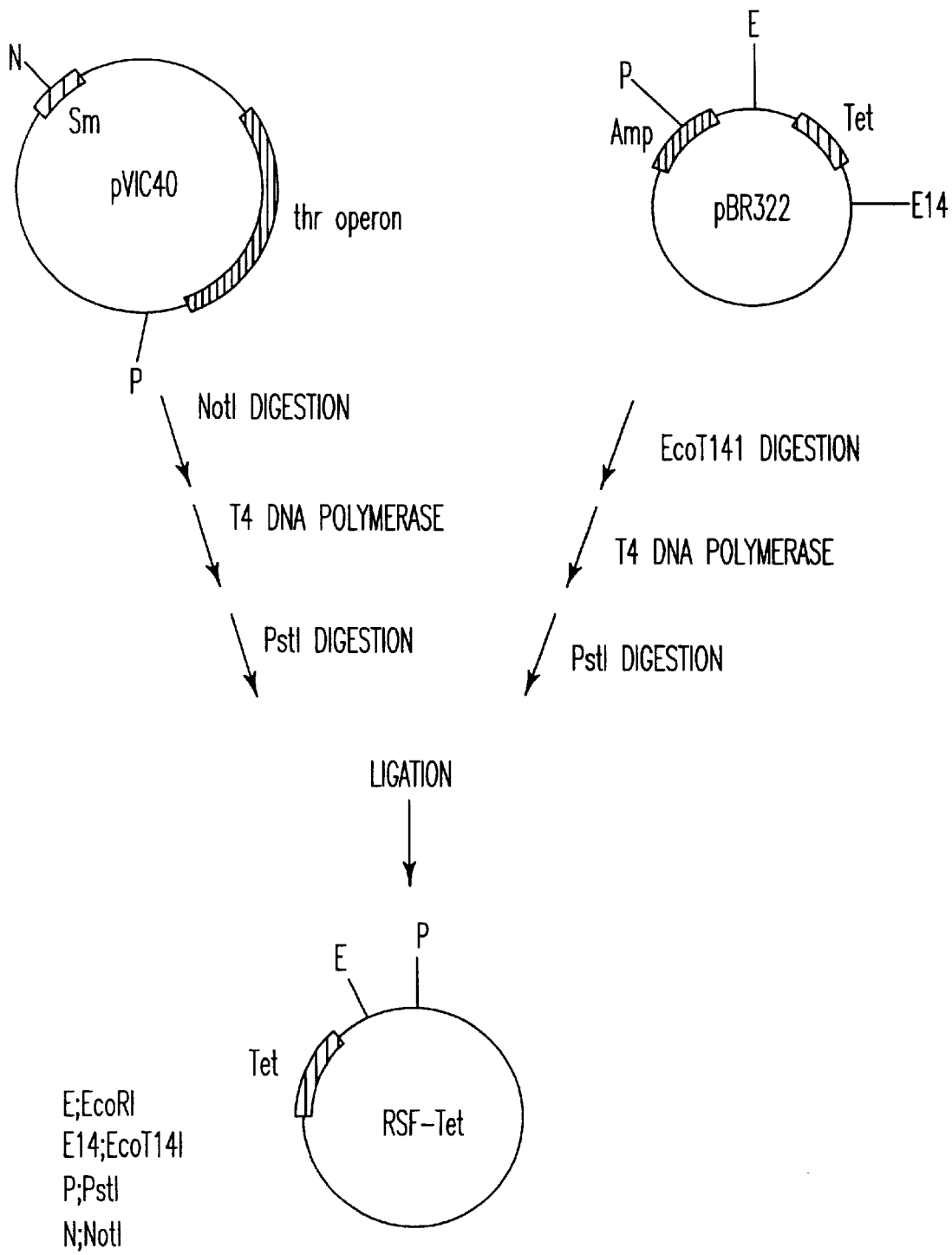
FIG. 3 shows construction of a plasmid RSF-Tet having a replication origin of a wide-host-range plasmid RSF1010 and a tetracycline resistance gene.

At the same time, a product obtained by digesting a plasmid pVIC40 having a replication origin of a wide-host-range plasmid RSF1010 (Japanese Patent Application Laid-Open (KOKAI) No. 8-047397(1996)) with NotI, followed by T4 DNA polymerase treatment and PstI digestion, and a product obtained by digesting pBR322 with EcoT141, followed by T4 DNA polymerase treatment and PstI digestion, were mixed and ligated with T4 ligase to obtain a plasmid RSF-Tet having the replication origin of RSF1010 and a tetracycline resistance gene (FIG. 3).

Figure 4:
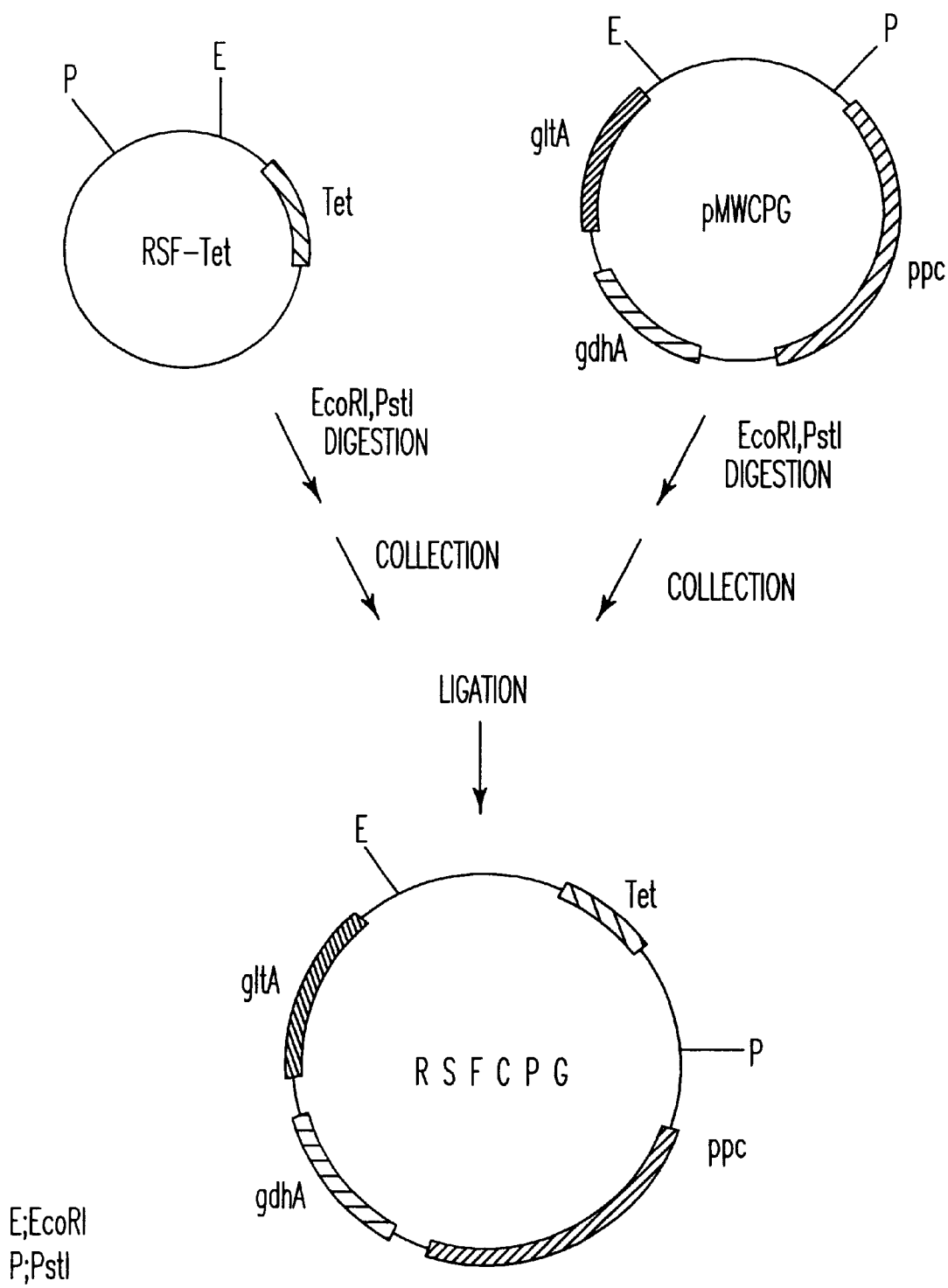
FIG. 4 shows construction of a plasmid RSFCPG having the replication origin of the wide-host-range plasmid RSF1010, the tetracycline resistance gene, the gltA gene, the ppc gene and the gdhA gene.

Then, the pMWCPG was digested with EcoRI and PstI, and a DNA fragment having the gltA gene, the ppc gene and the gdhA gene was purified and collected. Similarly, the RSF-Tet was digested with EcoRI and PstI, and a DNA fragment having the replication origin of RSF1010 was purified and collected. Those DNA fragments were mixed and ligated with T4 ligase to obtain a plasmid RSFCPG composed of RSF-Tet carrying the gltA gene, the ppc gene and the gdhA gene (FIG. 4). Expression of the gltA gene, the ppc gene and the gdhA gene by the resulting plasmid RSFCPG, and expression of the gdhA gene by the pSTVG were confirmed based on complementation of auxotrophy of *Escherichia coli* strains lacking the gltA gene, the ppc gene or the gdhA gene, and measurement of each enzyme activity.

Figure 5:
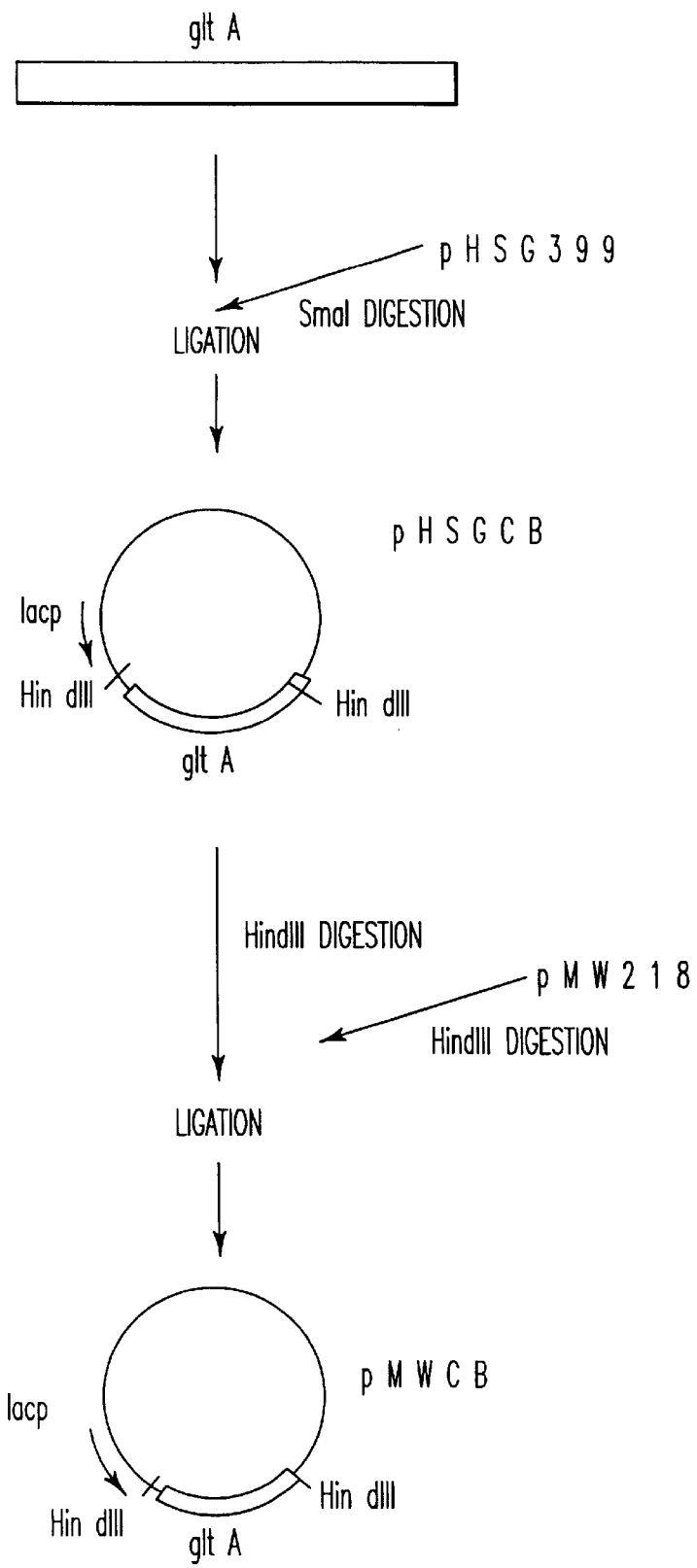
FIG. 5 shows construction of a plasmid pMWCB having the gltA gene.

A plasmid having a gltA gene derived from *Brevibacterium lactofermentum* was constructed as follows. PCR was performed by using primers having the nucleotide sequences represented in SEQ ID NOS: 6 and 7 selected based on the nucleotide sequence of the gltA gene of *Corynebacterium glutamicum* (Microbiology, 140, 1817–1828, 1994), and a chromosome DNA of *Brevibacterium lactofermentum* ATCC 13869 as a template to obtain a gltA gene fragment of about 3 kb. This fragment was inserted into a plasmid pHSG399 (purchased from Takara Shuzo) digested with SmaI to obtain a plasmid pHSGCB (FIG. 5). Then, the pHSGCB was digested with HindIII, and an excised gltA gene fragment of about 3 kb was inserted into a plasmid pMW218 (purchased from Nippon Gene) digested with HindIII to obtain a plasmid PMWCB (FIG. 5). Expression of the gltA gene by the resulting plasmid pMWCB was confirmed by determination of enzyme activity in the *Enterobacter agglomerans* AJ13355.

(2) Introduction of RSFCPG, pMWCB and pSTVG into *Enterobacter agglomerans* or *Serratia liquefacience*, and Evaluation of L-glutamic Acid Productivity The *Enterobacter agglomerans* ATCC 12287, the *Enterobacter agglomerans* AJ13355 and the *Serratia liquefacience* ATCC 14460 were transformed with the RSFCPG, pMWCB and pSTVG by electroporation (Miller J. H., "A Short Course in Bacterial Genetics; Handbook" Cold Spring Harbor Laboratory Press, USA, 1992) to obtain transformants exhibiting tetracycline resistance.

Each of the resulting transformants and the parent strains was inoculated into 50 ml-volume large size test tube containing 5 ml of a culture medium comprising 40 g/L glucose, 20 g/L ammonium sulfate, 0.5 g/L magnesium sulfate heptahydrate, 2 g/L potassium dihydrogenphosphate, 0.5 g/L sodium chloride, 0.25 g/L calcium chloride heptahydrate, 0.02 g/L ferrous sulfate heptahydrate, 0.02 g/L manganese sulfate tetrahydrate, 0.72 mg/L zinc sulfate dihydrate, 0.64 mg/L copper sulfate pentahydrate, 0.72 mg/L cobalt chloride hexahydrate, 0.4 mg/L boric acid, 1.2 mg/L sodium molybdate dihydrate, 2 g/L yeast extract, and 30 g/L calcium carbonate, and cultured at 37° C. with shaking until the glucose contained in the culture medium was consumed. However, as for the AJ13355/pMWCB strain and the AJ13355/pSTVG strain, the cultivation was stopped when about 10 g/L of glucose was consumed, i.e., cultivated for 15 hours like the parent strain AJ13355, because their glucose consumption rates were low. To the culture medium of the transformants, 25 mg/L of tetracycline was added. After the cultivation was completed, L-glutamic acid accumulated in the culture medium was measured. The results are shown in Table 1.

TABLE 1

| Accumulated amount of L-glutamic acid | |
|---|---|
| Bacterial strain | Accumulated amount of L-glutamic acid |
| ATCC12287 | 0.0 g/L |
| ATCC12287/RSFCPG | 6.1 |
| AJ13355 | 0.0 |
| AJ13355/RSFCPG | 3.3 |
| AJ13355/pMWCB | 0.8 |
| AJ13355/pSTVG | 0.8 |
| ATCC14460 | 0.0 |
| ATCC14460/RSFCPG | 2.8 |
| Culture medium alone | 0.2 |

While the *Enterobacter agglomerans* ATCC12287, the *Enterobacter agglomerans* AJ13355 and the *Serratia liquefacience* ATCC14460 did not accumulate L-glutamic acid, the strains whose CS, PEPC and GDH activities were amplified by introducing RSFCPG accumulated 6.1 g/L, 3.3 g/L, and 2.8 g/L of L-glutamic acid, respectively. The AJ13355 strain of which CS activity alone was amplified accumulated 0.8 g/L of L-glutamic acid, and the strain of which GDH activity alone was amplified also accumulated 0.8 g/L of L-glutamic acid.

(3) Cloning of αKGDH gene (referred to as "sucAB" hereinafter) of *Enterobacter agglomerans* AJ13355

The sucAB gene of the *Enterobacter agglomerans* AJ13355 was cloned by selecting a DNA fragment complementing acetate non-assimilation of an *Escherichia coli* strain lacking the αKGDH-E1 subunit gene (referred to as "sucA" hereinafter) from the chromosome DNA of the *Enterobacter agglomerans* AJ13355.

The chromosome DNA of the *Enterobacter agglomerans* AJ13355 strain was isolated by the same method as conventionally used for extracting chromosome DNA from *Escherichia coli* (Seibutsu Kogaku Jikken-sho (Textbook of Bioengineering Experiments), Ed. by the Society of Fermentation and Bioengineering, Japan, p.97–98, Baifukan, 1992). The pTWV228 used as the vector (ampicillin resistant) was a marketed product from Takara Shuzo.

Products obtained by digesting the chromosome DNA of the AJ13355 strain with EcoT221 and products obtained by digesting the pTWV228 with PstI were ligated by T4 ligase, and the *Escherichia coli* JRG465 lacking sucA (Herbert J. et al., Mol. Gen. Genetics, 1969, 105, p.182) was transformed with them. Strains grown on the acetic acid minimal medium were selected from the transformants obtained as described above, and a plasmid extracted from them was designated as pTWVEK101. The *Escherichia coli* JRG465 carrying the pTWVEK101 recovered the characteristics of acetate non-assimilability as well as auxotrophy for succinic acid or L-lysine and L-methionine. This suggests that the pTWVEK101 contains the sucA gene of *Enterobacter agglomerans*.

Figure 6:
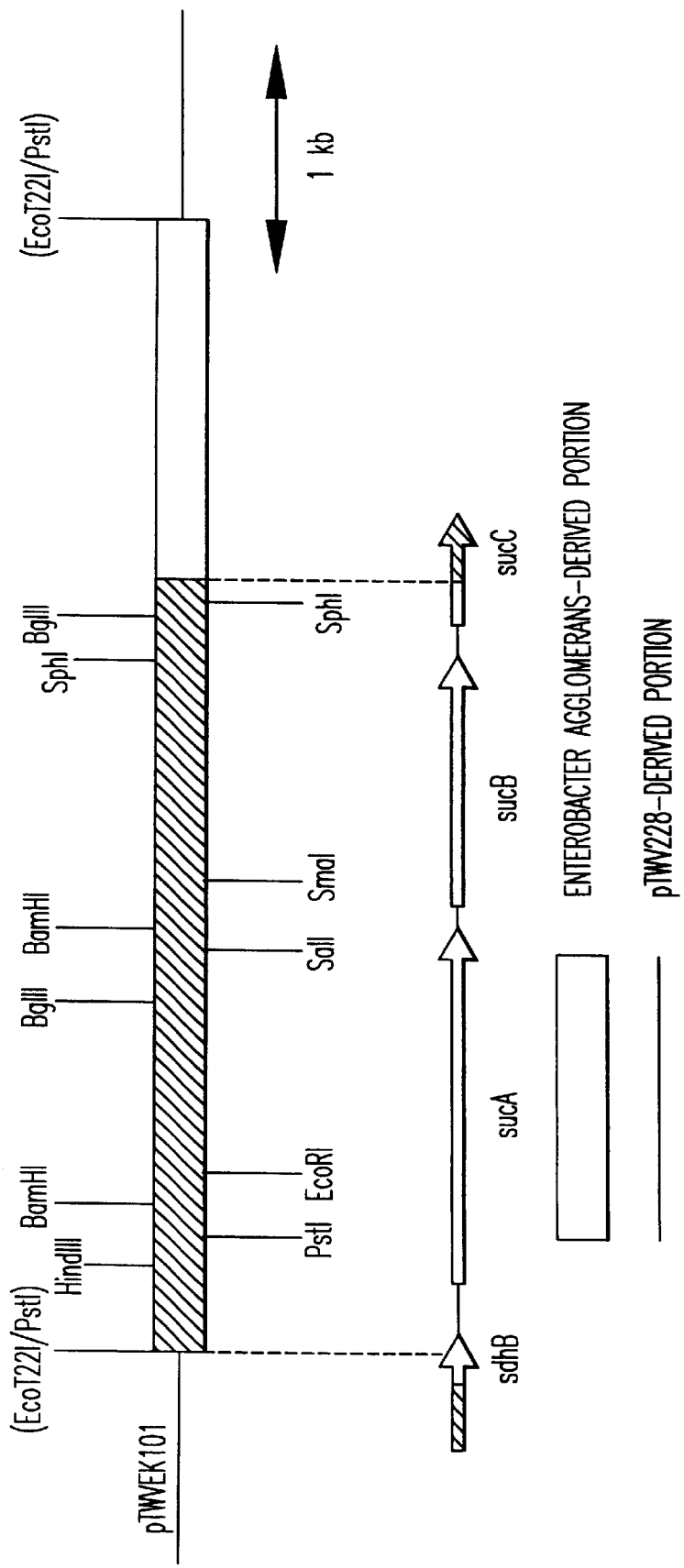
FIG. 6 shows a restriction map of a DNA fragment of pTWVEK101 derived from *Enterobacter agglomerans*.

A restriction map of *Enterobacter agglomerans*-derived DNA fragment of pTWVEK101 is shown in FIG. 6. The result of nucleotide sequencing of the hatched portion in FIG. 6 is shown in SEQ ID NO: 1. In this sequence, two full length ORFs and two nucleotides sequences considered as partial sequences of ORFs were found. Amino acid sequences that can be encoded by these ORFs and the partial sequences thereof are shown in SEQ ID NOS: 2 to 5 in order from the 5' ends. As a result of homology analysis of these sequences, it was found that the portion of which nucleotide sequence had been determined contained a 3' partial sequence of succinate dehydrogenase iron-sulfur protein gene (sdhB), full length sucA and αKGDH-E2 subunit gene (sucB gene), and 5' partial sequence of succinyl-CoA synthetase β subunit gene (sucC gene). Comparison of the amino acid sequences deduced from these nucleotide sequences with those of *Escherichia coli*. (Eur. J. Biochem., 141, 351–359 (1984), Eur. J. Biochem., 141, 361–374 (1984), and Biochemistry, 24, 6245–6252 (1985)) is shown in FIGS. 7 to 9. As shown by these results, the amino acid sequences exhibited markedly high homology. It was also found that a cluster of sdhB-sucA-sucB-sucC is formed on the *Enterobacter agglomerans* chromosome like *Escherichia coli* (Eur. J. Biochem., 141, 351–359 (1984), Eur. J. Biochem., 141, 361–374 (1984), and Biochemistry, 24, 6245–6252 (1985)).

(4) Acquisition of Strain Deficient in αKGDH Derived from *Enterobacter agglomerans* AJ13355

Using the sucAB gene of *Enterobacter agglomerans* obtained as described above, a strain lacking αKGDH of *Enterobacter agglomerans* was obtained by homologous recombination.

First, pTWVEK101 was digested with BglII to remove the C-terminus region corresponding to about half of the sucA gene and the full length of the sucB gene. To this site, a chloramphenicol resistance gene fragment cut out from the pHSG399 (Takara Shuzo) with AccI was then inserted. The region of sdhB-ΔsucAB::Cm$^r$-sucC obtained above was cut out with AflII and SacI. The resulting DNA fragment was used to transform the *Enterobacter agglomerans* AJ13355 strain by electroporation to obtain a chloramphenicol resistant strain, and thus a *Enterobacter agglomerans* AJ13356 strain lacking the sucAB gene where the sucAB gene on the chromosome was replaced by sucAB::Cm$^r$ was obtained.

To confirm that the AJ13356 strain obtained as described above was deficient in the αKGDH activity, its enzymatic activity was determined by the method of Reed (L. J. Reed and B. B. Mukherjee, Methods in Enzymology 1969, 13, p.55–61). As a result, the αKGDH activity could not be detected in the AJ13356 strain as shown in Table 2, and thus it was confirmed that the strain lacked the sucAB as desired.

TABLE 2

| | αKGDH activity | |
|---|---|---|
| Bacterial strain | | αKGDH activity (ΔABS /min/mg protein) |
| AJ13355 | | 0.481 |
| AJ13356 | | <0.0001 |

(5) Evaluation of L-glutamic Acid Productivity of *Enterobacter agglomerans* Strain Deficient in αKGDH Each of the AJ13355 and AJ13356 strains was inoculated into a 500 ml-volume flask containing 20 ml of a culture medium comprising 40 g/L glucose, 20 g/L ammonium sulfate, 0.5 g/L magnesium sulfate heptahydrate, 2 g/L potassium dihydrogenphosphate, 0.5 g/L sodium chloride, 0.25 g/L calcium chloride heptahydrate, 0.02 g/L ferrous sulfate heptahydrate, 0.02 g/L manganese sulfate tetrahydrate, 0.72 mg/L zinc sulfate dihydrate, 0.64 mg/L copper sulfate pentahydrate, 0.72 mg/L cobalt chloride hexahydrate, 0.4 mg/L boric acid, 1.2 mg/L sodium molybdate dihydrate, 2 g/L yeast extract, 30 g/L calcium carbonate, 200 mg/L L-lysine monohydrochlorida, 200 mg/L L-methionine and 200 mg/L DL-α,ε-diaminopimelic acid (DAP), and cultured at 37° C. with shaking until the glucose contained in the culture medium was consumed. After the cultivation was completed, L-glutamic acid and α-ketoglutaric acid (abbreviated as "αKG" hereinafter) accumulated in the culture medium were measured. The results are shown in Table 3.

TABLE 3

| Accumulated amounts of L-glutamic acid and αKG | | |
|---|---|---|
| Bacterial strain | Accumulated amount of L-glutamic acid | Accumulated amount of αKG |
| AJ13355 | 0.0 g/L | 0.0 g/L |
| AJ13356 | 1.5 | 3.2 |

The AJ13356 strain deficient in the αKGDH activity accumulated 1.5 g/L of L-glutamic acid, and simultaneously accumulated 3.2 g/L of αKG.

(6) Introduction of RSFCPG into *Enterobacter agglomerans* Strain Lacking αKGDH and Evaluation of L-glutamic Acid Productivity The AJ13356 strain was transformed with the RSFCPG, and the resulting strain introduced with the RSFCPG, AJ13356/RSFCPG, was inoculated into a 500 ml-volume flask containing 20 ml of a culture medium comprising 40 g/L glucose, 20 g/L ammonium sulfate, 0.5 g/L magnesium sulfate heptahydrate, 2 g/L potassium dihydrogenphosphate, 0.5 g/L sodium chloride, 0.25 g/L calcium chloride heptahydrate, 0.02 g/L ferrous sulfate heptahydrate, 0.02 g/L manganese sulfate tetrahydrate, 0.72 mg/L zinc sulfate dihydrate, 0.64 mg/L copper sulfate pentahydrate, 0.72 mg/L cobalt chloride hexahydrate, 0.4 mg/L boric acid, 1.2 mg/L sodium molybdate dihydrate, 2 g/L yeast extract, 25 mg/L tetracycline, 30 g/L calcium carbonate, 200 mg/L L-lysine monohydrochloride, 200 mg/L L-methionine and 200 mg/L DL-α,ε-DAP, and cultured at 37° C. with shaking until the glucose contained in the culture medium was consumed. After the cultivation was completed, L-glutamic acid and αKG accumulated in the culture medium were measured.

The results are shown in Table 4.

TABLE 4

| Accumulated amounts of L-glutamic acid and αKG | | |
|---|---|---|
| Bacterial strain | Accumulated amount of L-glutamic acid | Accumulated amount of αKG |
| AJ13356 | 1.4 g/L | 2.9 g/L |
| AJ13356/RSFCPG | 5.1 | 0.0 |

In the strain of which CS, PEPC and GDH activities were amplified by the introduction of RSFCPG, the accumulated amount of αKG was reduced, and the accumulated amount of L-glutamic acid was further improved.

What is claimed is:

1. A microorganism belonging to the genus Enterobacter or Serratia and having (1) an ability to produce L-glutamic acid in a culture medium, (2) and having the following properties:
   (a) the microorganism has an increased activity of at least one enzyme selected from the group consisting of citrate synthase, phosphoenolpyruvate carboxylase, and glutamate dehydrogenase; and
   (b) the microorganism has decreased activity of α-ketoglutarate dehydrogenase.

2. The microorganism of claim 1, which has increased activity of the citrate synthase, phosphoenolpyruvate carboxylase, and glutamate dehydrogenase.

3. The microorganism of claim 1, which is *Enterbacter agglomerans* or *Serratia liquefacience*.

4. The microorganism of claim 1, which is transformed with a vector containing a nucleic acid encoding at least one enzyme selected from the group consisting of citrate synthase, phosphoenolpyruvate carboxylase, and glutamate dehydrogenase.

5. The microoganism of claim 1, which is transformed with at least one vector containing a nucleic acid encoding citrate synthase, phosphoenolpyruvate carboxylase, and glutamate dehydrogenase.

6. The microogranism of claim 1, wherein a gene encoding said α-ketoglutarate dehydrogenase has been mutagenized to decrease the activity of the α-ketoglutarate dehydrogenase.

7. A method for producing L-glutamic acid, comprising:
culturing the microorganism of claim 1 in a liquid culture medium to produce and accumulate L-glutamic acid culture medium, and
collecting the L-glutamic acid from the culture medium.

8. A method for producing L-glutamic acid, comprising:
culturing the microorganism of claim 2 in a liquid culture medium to produce and accumulate L-glutamic acid culture medium, and
collecting the L-glutamic acid from the culture medium.

9. A method for producing L-glutamic acid, comprising:
culturing the microorganism of claim 3 in a liquid culture medium to produce and accumulate L-glutamic acid culture medium, and
collecting the L-glutamic acid from the culture medium.

10. A method for producing L-glutamic acid, comprising:
culturing the microorganism of claim 4 in a liquid culture medium to produce and accumulate L-glutamic acid culture medium, and
collecting the L-glutamic acid from the culture medium.

11. A method for producing L-glutamic acid, comprising:
culturing the microorganism of claim 5 in a liquid culture medium to produce and accumulate L-glutamic acid culture medium, and
collecting the L-glutamic acid from the culture medium.

12. A method for producing L-glutamic acid, comprising:
culturing the microorganism of claim 6 in a liquid culture medium to produce and accumulate L-glutamic acid culture medium, and
collecting the L-glutamic acid from the culture medium.

* * * * *

SEQUENCE LISTING

<160> NUMBER OF SEQ ID NOS: 15

<210> SEQ ID NO 1
<211> LENGTH: 4556
<212> TYPE: DNA
<213> ORGANISM: Enterobacter agglomerans
<220> FEATURE:
<221> NAME/KEY: CDS
<222> LOCATION: (2)..(121)
<223> OTHER INFORMATION:
<221> NAME/KEY: CDS
<222> LOCATION: (322)..(3129)
<223> OTHER INFORMATION:
<221> NAME/KEY: CDS
<222> LOCATION: (3145)..(4368)
<223> OTHER INFORMATION:
<221> NAME/KEY: CDS
<222> LOCATION: (4437)..(4556)
<223> OTHER INFORMATION:

<400> SEQUENCE: 1

```
t gca ttc agc gtt ttc cgc tgt cac agc atc atg aac tgt gta agt gtt        49
  Ala Phe Ser Val Phe Arg Cys His Ser Ile Met Asn Cys Val Ser Val
  1               5                  10                  15 tgt cct aaa ggg cta aac ccg acg cgc gct atc ggc cac att aag tcg          97
Cys Pro Lys Gly Leu Asn Pro Thr Arg Ala Ile Gly His Ile Lys Ser
            20                  25                  30 atg ctg ctg caa cgc agc gcg tag ttataccacc gggaacctca ggttcccggt        151
Met Leu Leu Gln Arg Ser Ala
        35 attttacgga agcctctgta aacgcggtcc caaccacgtt tacaaaggtt cccttacggg        211 ccgggcgcgc gctgcgcaca gtgctcgtat cgctgaactc actacggcaa accgcgaaag        271 cggcaacaaa tgaaacctca aaaagcata acattgctta agggatcaca atg cag           327
                                                          Met Gln
                                                           40 aac agc gcg atg aag ccc tgg ctg gac tcc tcc tgg ctg gcc ggc gcg         375
Asn Ser Ala Met Lys Pro Trp Leu Asp Ser Ser Trp Leu Ala Gly Ala
                45                  50                  55 aat cag tct tac ata gag caa ctc tat gag gat ttc ctg acc gat cct         423
Asn Gln Ser Tyr Ile Glu Gln Leu Tyr Glu Asp Phe Leu Thr Asp Pro
        60                  65                  70 gac tct gtg gat gca gtg tgg cgc tcg atg ttc caa cag tta cca ggc         471
Asp Ser Val Asp Ala Val Trp Arg Ser Met Phe Gln Gln Leu Pro Gly
    75                  80                  85 acg gga gtg aaa cct gag cag ttc cac tcc gca act cgc gaa tat ttc         519
```

```
                                                                            -continued Thr Gly Val Lys Pro Glu Gln Phe His Ser Ala Thr Arg Glu Tyr Phe
 90              95                 100                 105 cgt cgc ctg gcg aaa gac gca tct cgt tac acc tcc tca gtt acc gat             567
Arg Arg Leu Ala Lys Asp Ala Ser Arg Tyr Thr Ser Ser Val Thr Asp
                110                 115                 120 ccg gca acc aac tcc aaa caa gtg aaa gtg ctg cag ctg att aac gcg             615
Pro Ala Thr Asn Ser Lys Gln Val Lys Val Leu Gln Leu Ile Asn Ala
            125                 130                 135 ttt cgt ttc cgc gga cat cag gaa gca aat ctc gat ccg ctt ggc ctg             663
Phe Arg Phe Arg Gly His Gln Glu Ala Asn Leu Asp Pro Leu Gly Leu
        140                 145                 150 tgg aaa cag gac cgc gtt gcc gat ctc gat cct gcc ttt cac gat ctg             711
Trp Lys Gln Asp Arg Val Ala Asp Leu Asp Pro Ala Phe His Asp Leu
    155                 160                 165 acc gac gcc gat ttt cag gaa agc ttt aac gta ggt tct ttt gcc att             759
Thr Asp Ala Asp Phe Gln Glu Ser Phe Asn Val Gly Ser Phe Ala Ile
170                 175                 180                 185 ggc aaa gaa acc atg aag ctg gcc gat ctg ttc gac gcg ctg aag cag             807
Gly Lys Glu Thr Met Lys Leu Ala Asp Leu Phe Asp Ala Leu Lys Gln
                190                 195                 200 acc tac tgt ggc tcg att ggt gca gag tat atg cac atc aat aac acc             855
Thr Tyr Cys Gly Ser Ile Gly Ala Glu Tyr Met His Ile Asn Asn Thr
            205                 210                 215 gaa gag aaa cgc tgg atc cag cag cgt atc gaa tcc ggt gcg agc cag             903
Glu Glu Lys Arg Trp Ile Gln Gln Arg Ile Glu Ser Gly Ala Ser Gln
        220                 225                 230 acg tca ttc agt ggc gaa gag aaa aaa ggt ttc ctg aaa gag ctg acc             951
Thr Ser Phe Ser Gly Glu Glu Lys Lys Gly Phe Leu Lys Glu Leu Thr
    235                 240                 245 gcg gca gaa ggg ctg gaa aaa tat ctg ggc gcg aaa ttc ccg ggt gca             999
Ala Ala Glu Gly Leu Glu Lys Tyr Leu Gly Ala Lys Phe Pro Gly Ala
250                 255                 260                 265 aaa cgt ttc tcg ctg gaa ggc ggt gat gcg ctg gtg ccg atg ctg cgc            1047
Lys Arg Phe Ser Leu Glu Gly Gly Asp Ala Leu Val Pro Met Leu Arg
                270                 275                 280 gag atg att cgt cat gcg ggc aaa agc ggc aca cgt gaa gtg gta ctg            1095
Glu Met Ile Arg His Ala Gly Lys Ser Gly Thr Arg Glu Val Val Leu
            285                 290                 295 ggg atg gcg cac cgt ggc cgt ctt aac gta ctg att aac gta ctg ggt            1143
Gly Met Ala His Arg Gly Arg Leu Asn Val Leu Ile Asn Val Leu Gly
        300                 305                 310 aaa aag cca cag gat ctg ttc gac gaa ttc tcc ggt aaa cac aaa gag            1191
Lys Lys Pro Gln Asp Leu Phe Asp Glu Phe Ser Gly Lys His Lys Glu
    315                 320                 325 cat ctg ggc acc ggt gat gtg aag tat cac atg ggc ttc tct tcg gat            1239
His Leu Gly Thr Gly Asp Val Lys Tyr His Met Gly Phe Ser Ser Asp
330                 335                 340                 345 att gaa acc gaa ggt ggt ctg gtg cat ctg gcg ctg gcg ttt aac ccg            1287
Ile Glu Thr Glu Gly Gly Leu Val His Leu Ala Leu Ala Phe Asn Pro
                350                 355                 360 tct cac ctg gaa att gtc agc ccg gtg gtc atg gga tcg gta cgt gca            1335
Ser His Leu Glu Ile Val Ser Pro Val Val Met Gly Ser Val Arg Ala
            365                 370                 375 cgt ctc gat cgt ctg gcc gaa ccg gtc agc aat aaa gtg ttg cct atc            1383
Arg Leu Asp Arg Leu Ala Glu Pro Val Ser Asn Lys Val Leu Pro Ile
        380                 385                 390 acc att cac ggt gat gcg gcg gtg att ggt cag ggc gtg gtt cag gaa            1431
Thr Ile His Gly Asp Ala Ala Val Ile Gly Gln Gly Val Val Gln Glu
    395                 400                 405
```

-continued

| | |
|---|---|
| acc ctg aac atg tct cag gcg cgc ggc tac gaa gtg ggc ggc acg gta<br>Thr Leu Asn Met Ser Gln Ala Arg Gly Tyr Glu Val Gly Gly Thr Val<br>410                        415                    420                    425 | 1479 |
| cgt atc gtc att aac aac cag gtt ggt ttt acc acc tcc aac ccg aaa<br>Arg Ile Val Ile Asn Asn Gln Val Gly Phe Thr Thr Ser Asn Pro Lys<br>                    430                    435                    440 | 1527 |
| gat gcg cgt tca acc ccg tac tgt act gac atc ggc aag atg gtg ctg<br>Asp Ala Arg Ser Thr Pro Tyr Cys Thr Asp Ile Gly Lys Met Val Leu<br>            445                    450                    455 | 1575 |
| gca ccg att ttc cac gtc aat gct gac gat ccg gaa gcg gtg gcc ttt<br>Ala Pro Ile Phe His Val Asn Ala Asp Asp Pro Glu Ala Val Ala Phe<br>460                        465                    470 | 1623 |
| gtt acc cgc ctg gcg ctg gac tat cgc aac acc ttc aaa cgc gat gtg<br>Val Thr Arg Leu Ala Leu Asp Tyr Arg Asn Thr Phe Lys Arg Asp Val<br>            475                    480                    485 | 1671 |
| ttt atc gat ctg gtg tgc tat cgc cgt cat ggt cac aac gag gcg gat<br>Phe Ile Asp Leu Val Cys Tyr Arg Arg His Gly His Asn Glu Ala Asp<br>490                        495                    500                    505 | 1719 |
| gag cca agt gct acc cag ccg ttg atg tac cag aaa atc aaa aag cat<br>Glu Pro Ser Ala Thr Gln Pro Leu Met Tyr Gln Lys Ile Lys Lys His<br>                    510                    515                    520 | 1767 |
| ccg acg ccg cgt aaa att tac gcc gat cgt ctg gaa ggc gaa ggt gtc<br>Pro Thr Pro Arg Lys Ile Tyr Ala Asp Arg Leu Glu Gly Glu Gly Val<br>            525                    530                    535 | 1815 |
| gcg tcg cag gaa gat gcc acc gag atg gtg aac ctg tac cgc gat gcg<br>Ala Ser Gln Glu Asp Ala Thr Glu Met Val Asn Leu Tyr Arg Asp Ala<br>540                        545                    550 | 1863 |
| ctc gat gcg ggc gaa tgc gtg gtg ccg gaa tgg cgt ccg atg agc ctg<br>Leu Asp Ala Gly Glu Cys Val Val Pro Glu Trp Arg Pro Met Ser Leu<br>555                        560                    565 | 1911 |
| cac tcc ttc acg tgg tcg cct tat ctg aac cac gaa tgg gat gag cct<br>His Ser Phe Thr Trp Ser Pro Tyr Leu Asn His Glu Trp Asp Glu Pro<br>570                        575                    580                    585 | 1959 |
| tat ccg gca cag gtt gac atg aaa cgc ctg aag gaa ctg gca ttg cgt<br>Tyr Pro Ala Gln Val Asp Met Lys Arg Leu Lys Glu Leu Ala Leu Arg<br>                    590                    595                    600 | 2007 |
| atc agc cag gtc cct gag cag att gaa gtg cag tcg cgc gtg gcc aag<br>Ile Ser Gln Val Pro Glu Gln Ile Glu Val Gln Ser Arg Val Ala Lys<br>            605                    610                    615 | 2055 |
| atc tat aac gat cgc aag ctg atg gcc gaa ggc gag aaa gcg ttc gac<br>Ile Tyr Asn Asp Arg Lys Leu Met Ala Glu Gly Glu Lys Ala Phe Asp<br>                    620                    625                    630 | 2103 |
| tgg ggc ggt gcc gag aat ctg gcg tac gcc acg ctg gtg gat gaa ggt<br>Trp Gly Gly Ala Glu Asn Leu Ala Tyr Ala Thr Leu Val Asp Glu Gly<br>635                        640                    645 | 2151 |
| att ccg gtt cgc ctc tcg ggt gaa gac tcc ggt cgt gga acc ttc ttc<br>Ile Pro Val Arg Leu Ser Gly Glu Asp Ser Gly Arg Gly Thr Phe Phe<br>650                        655                    660                    665 | 2199 |
| cat cgc cac gcg gtc gtg cac aac cag gct aac ggt tca acc tat acg<br>His Arg His Ala Val Val His Asn Gln Ala Asn Gly Ser Thr Tyr Thr<br>                    670                    675                    680 | 2247 |
| ccg ctg cac cat att cat aac agc cag ggc gag ttc aaa gtc tgg gat<br>Pro Leu His His Ile His Asn Ser Gln Gly Glu Phe Lys Val Trp Asp<br>            685                    690                    695 | 2295 |
| tcg gtg ctg tct gaa gaa gcg gtg ctg gcg ttt gaa tac ggt tac gcc<br>Ser Val Leu Ser Glu Glu Ala Val Leu Ala Phe Glu Tyr Gly Tyr Ala<br>700                        705                    710 | 2343 |
| acg gct gag ccg cgc gtg ctg acc atc tgg gaa gcg cag ttt ggt gac<br>Thr Ala Glu Pro Arg Val Leu Thr Ile Trp Glu Ala Gln Phe Gly Asp<br>715                        720                    725 | 2391 |

```
ttt gcc aac ggt gct cag gtg gtg att gac cag ttc atc agc tct ggc    2439
Phe Ala Asn Gly Ala Gln Val Val Ile Asp Gln Phe Ile Ser Ser Gly
730             735                 740                 745 gaa cag aag tgg ggc cgt atg tgt ggc ctg gtg atg ttg ctg ccg cat    2487
Glu Gln Lys Trp Gly Arg Met Cys Gly Leu Val Met Leu Leu Pro His
            750                 755                 760 ggc tac gaa ggt cag gga ccg gaa cac tcc tct gcc cgt ctg gaa cgc    2535
Gly Tyr Glu Gly Gln Gly Pro Glu His Ser Ser Ala Arg Leu Glu Arg
        765                 770                 775 tat ctg caa ctt tgc gcc gag cag aac atg cag gtt tgc gtc ccg tcg    2583
Tyr Leu Gln Leu Cys Ala Glu Gln Asn Met Gln Val Cys Val Pro Ser
    780                 785                 790 acg ccg gct cag gtg tat cac atg ctg cgc cgt cag gcg ctg cgc ggg    2631
Thr Pro Ala Gln Val Tyr His Met Leu Arg Arg Gln Ala Leu Arg Gly
795                 800                 805 atg cgc cgt ccg ctg gtg gtg atg tcg ccg aag tcg ctg tta cgc cat    2679
Met Arg Arg Pro Leu Val Val Met Ser Pro Lys Ser Leu Leu Arg His
810                 815                 820                 825 cca ctg gcg atc tcg tcg ctg gat gaa ctg gca aac ggc agt ttc cag    2727
Pro Leu Ala Ile Ser Ser Leu Asp Glu Leu Ala Asn Gly Ser Phe Gln
            830                 835                 840 ccg gcc att ggt gag atc gac gat ctg gat ccg cag ggc gtg aaa cgc    2775
Pro Ala Ile Gly Glu Ile Asp Asp Leu Asp Pro Gln Gly Val Lys Arg
        845                 850                 855 gtc gtg ctg tgc tcc ggt aag gtt tac tac gat ctg ctg gaa cag cgt    2823
Val Val Leu Cys Ser Gly Lys Val Tyr Tyr Asp Leu Leu Glu Gln Arg
    860                 865                 870 cgt aaa gac gag aaa acc gat gtt gcc atc gtg cgc atc gaa cag ctt    2871
Arg Lys Asp Glu Lys Thr Asp Val Ala Ile Val Arg Ile Glu Gln Leu
875                 880                 885 tac ccg ttc ccg cat cag gcg gta cag gaa gca ttg aaa gcc tat tct    2919
Tyr Pro Phe Pro His Gln Ala Val Gln Glu Ala Leu Lys Ala Tyr Ser
890                 895                 900                 905 cac gta cag gac ttt gtc tgg tgc cag gaa gag cct ctg aac cag ggc    2967
His Val Gln Asp Phe Val Trp Cys Gln Glu Glu Pro Leu Asn Gln Gly
            910                 915                 920 gcc tgg tac tgt agc cag cat cat ttc cgt gat gtc gtg ccg ttt ggt    3015
Ala Trp Tyr Cys Ser Gln His His Phe Arg Asp Val Val Pro Phe Gly
        925                 930                 935 gcc acc ctg cgt tat gca ggt cgc ccg gca tcg gct tct ccg gcc gtg    3063
Ala Thr Leu Arg Tyr Ala Gly Arg Pro Ala Ser Ala Ser Pro Ala Val
    940                 945                 950 ggt tat atg tcc gta cac caa caa cag cag caa gac ctg gtt aat gac    3111
Gly Tyr Met Ser Val His Gln Gln Gln Gln Gln Asp Leu Val Asn Asp
955                 960                 965 gca ctg aac gtc aat taa ttaaaaggaa agata atg agt agc gta gat att   3162
Ala Leu Asn Val Asn                       Met Ser Ser Val Asp Ile
970                                       975                 980 ctc gtt ccc gac ctg cct gaa tcg gtt gca gat gcc aca gta gca acc    3210
Leu Val Pro Asp Leu Pro Glu Ser Val Ala Asp Ala Thr Val Ala Thr
            985                 990                 995 tgg cac aag aaa cca ggc gat gca gtc agc cgc gat gaa gtc atc        3255
Trp His Lys Lys Pro Gly Asp Ala Val Ser Arg Asp Glu Val Ile
            1000                1005                1010 gtc gaa att gaa act gac aaa gtc gtg ctg gaa gtg ccg gca tct        3300
Val Glu Ile Glu Thr Asp Lys Val Val Leu Glu Val Pro Ala Ser
            1015                1020                1025 gcc gat ggc gtg ctg gaa gcc gtg ctg gaa gac gaa ggg gca acc        3345
Ala Asp Gly Val Leu Glu Ala Val Leu Glu Asp Glu Gly Ala Thr
```

```
                1030              1035              1040
gtt acg tcc cgc cag atc ctg ggt cgc ctg aaa gaa ggc aac agt         3390
Val Thr Ser Arg Gln Ile Leu Gly Arg Leu Lys Glu Gly Asn Ser
                1045              1050              1055 gcg ggt aaa gaa agc agt gcc aaa gcg gaa agc aat gac acc acg         3435
Ala Gly Lys Glu Ser Ser Ala Lys Ala Glu Ser Asn Asp Thr Thr
                1060              1065              1070 cca gcc cag cgt cag aca gcg tcg ctt gaa gaa gag agc agc gat         3480
Pro Ala Gln Arg Gln Thr Ala Ser Leu Glu Glu Glu Ser Ser Asp
                1075              1080              1085 gcg ctc agc ccg gcg atc cgt cgc ctg att gcg gag cat aat ctt         3525
Ala Leu Ser Pro Ala Ile Arg Arg Leu Ile Ala Glu His Asn Leu
                1090              1095              1100 gac gct gcg cag atc aaa ggc acc ggc gta ggc gga cgt tta acg         3570
Asp Ala Ala Gln Ile Lys Gly Thr Gly Val Gly Gly Arg Leu Thr
                1105              1110              1115 cgt gaa gac gtt gaa aaa cat ctg gcg aac aaa ccg cag gct gag         3615
Arg Glu Asp Val Glu Lys His Leu Ala Asn Lys Pro Gln Ala Glu
                1120              1125              1130 aaa gcc gcc gcg cca gcg gcg ggt gca gca acg gct cag cag cct         3660
Lys Ala Ala Ala Pro Ala Ala Gly Ala Ala Thr Ala Gln Gln Pro
                1135              1140              1145 gtt gcc aac cgc agc gaa aaa cgt gtt ccg atg acg cgt tta cgt         3705
Val Ala Asn Arg Ser Glu Lys Arg Val Pro Met Thr Arg Leu Arg
                1150              1155              1160 aag cgc gtc gcg gag cgt ctg ctg gaa gcc aag aac agc acc gcc         3750
Lys Arg Val Ala Glu Arg Leu Leu Glu Ala Lys Asn Ser Thr Ala
                1165              1170              1175 atg ttg acg acc ttc aac gaa atc aac atg aag ccg att atg gat         3795
Met Leu Thr Thr Phe Asn Glu Ile Asn Met Lys Pro Ile Met Asp
                1180              1185              1190 ctg cgt aag cag tac ggc gat gcg ttc gag aag cgt cac ggt gtg         3840
Leu Arg Lys Gln Tyr Gly Asp Ala Phe Glu Lys Arg His Gly Val
                1195              1200              1205 cgt ctg ggc ttt atg tct ttc tac atc aag gcc gtg gtc gaa gcg         3885
Arg Leu Gly Phe Met Ser Phe Tyr Ile Lys Ala Val Val Glu Ala
                1210              1215              1220 ctg aag cgt tat cca gaa gtc aac gcc tct atc gat ggc gaa gac         3930
Leu Lys Arg Tyr Pro Glu Val Asn Ala Ser Ile Asp Gly Glu Asp
                1225              1230              1235 gtg gtg tac cac aac tat ttc gat gtg agt att gcc gtc tct acg         3975
Val Val Tyr His Asn Tyr Phe Asp Val Ser Ile Ala Val Ser Thr
                1240              1245              1250 cca cgc gga ctg gtg acg cct gtc ctg cgt gac gtt gat gcg ctg         4020
Pro Arg Gly Leu Val Thr Pro Val Leu Arg Asp Val Asp Ala Leu
                1255              1260              1265 agc atg gct gac atc gag aag aaa att aaa gaa ctg gca gtg aaa         4065
Ser Met Ala Asp Ile Glu Lys Lys Ile Lys Glu Leu Ala Val Lys
                1270              1275              1280 ggc cgt gac ggc aag ctg acg gtt gac gat ctg acg ggc ggt aac         4110
Gly Arg Asp Gly Lys Leu Thr Val Asp Asp Leu Thr Gly Gly Asn
                1285              1290              1295 ttt acc atc acc aac ggt ggt gtg ttc ggt tcg ctg atg tct acg         4155
Phe Thr Ile Thr Asn Gly Gly Val Phe Gly Ser Leu Met Ser Thr
                1300              1305              1310 cca atc atc aac ccg cca cag agc gcg att ctg ggc atg cac gcc         4200
Pro Ile Ile Asn Pro Pro Gln Ser Ala Ile Leu Gly Met His Ala
                1315              1320              1325 att aaa gat cgt cct atg gcg gtc aat ggt cag gtt gtg atc ctg         4245
```

```
Ile Lys Asp Arg  Pro Met Ala Val  Asn Gly Gln Val  Val Ile Leu
         1330               1335                1340 cca atg atg tac  ctg gct ctc tcc  tac gat cac cgt  tta atc gat            4290
Pro Met Met Tyr  Leu Ala Leu Ser  Tyr Asp His Arg  Leu Ile Asp
         1345               1350                1355 ggt cgt gaa tct  gtc ggc tat ctg  gtc gcg gtg aaa  gag atg ctg            4335
Gly Arg Glu Ser  Val Gly Tyr Leu  Val Ala Val Lys  Glu Met Leu
         1360               1365                1370 gaa gat ccg gcg  cgt ctg ctg ctg  gat gtc tga ttcatcactg                  4378
Glu Asp Pro Ala  Arg Leu Leu Leu  Asp Val
         1375               1380 ggcacgcgtt gcgtgcccaa tctcaatact cttttcagat ctgaatggat agaacatc           4436 atg aac tta cac  gaa tac cag gct  aaa cag ctg ttt  gca cgg tat            4481
Met Asn Leu His  Glu Tyr Gln Ala  Lys Gln Leu Phe  Ala Arg Tyr
         1385               1390                1395 ggc atg cca gca  ccg acc ggc tac  gcc tgt act aca  cca cgt gaa            4526
Gly Met Pro Ala  Pro Thr Gly Tyr  Ala Cys Thr Thr  Pro Arg Glu
         1400               1405                1410 gca gaa gaa gcg  gca tcg aaa atc  ggt gca                                 4556
Ala Glu Glu Ala  Ala Ser Lys Ile  Gly Ala
         1415               1420
```

<210> SEQ ID NO 2
<211> LENGTH: 39
<212> TYPE: PRT
<213> ORGANISM: Enterobacter agglomerans

<400> SEQUENCE: 2

```
Ala Phe Ser Val Phe Arg Cys His Ser Ile Met Asn Cys Val Ser Val
1               5                   10                  15

Cys Pro Lys Gly Leu Asn Pro Thr Arg Ala Ile Gly His Ile Lys Ser
            20                  25                  30

Met Leu Leu Gln Arg Ser Ala
        35
```

<210> SEQ ID NO 3
<211> LENGTH: 935
<212> TYPE: PRT
<213> ORGANISM: Enterobacter agglomerans

<400> SEQUENCE: 3

```
Met Gln Asn Ser Ala Met Lys Pro Trp Leu Asp Ser Ser Trp Leu Ala
1               5                   10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45

Pro Gly Thr Gly Val Lys Pro Gln Phe His Ser Ala Thr Arg Glu
    50                  55                  60

Tyr Phe Arg Arg Leu Ala Lys Asp Ala Ser Arg Tyr Thr Ser Ser Val
65                  70                  75                  80

Thr Asp Pro Ala Thr Asn Ser Lys Gln Val Lys Val Leu Gln Leu Ile
                85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

Asp Leu Thr Asp Ala Asp Phe Gln Glu Ser Phe Asn Val Gly Ser Phe
```

```
        130                 135                 140
Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn
                165                 170                 175

Asn Thr Glu Glu Lys Arg Trp Ile Gln Gln Arg Ile Glu Ser Gly Ala
            180                 185                 190

Ser Gln Thr Ser Phe Ser Gly Glu Glu Lys Lys Gly Phe Leu Lys Glu
            195                 200                 205

Leu Thr Ala Ala Glu Gly Leu Glu Lys Tyr Leu Gly Ala Lys Phe Pro
            210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
                245                 250                 255

Val Leu Gly Met Ala His Arg Gly Arg Leu Asn Val Leu Ile Asn Val
                260                 265                 270

Leu Gly Lys Lys Pro Gln Asp Leu Phe Asp Glu Phe Ser Gly Lys His
            275                 280                 285

Lys Glu His Leu Gly Thr Gly Asp Val Lys Tyr His Met Gly Phe Ser
        290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Val Met Gly Ser Val
                325                 330                 335

Arg Ala Arg Leu Asp Arg Leu Ala Glu Pro Val Ser Asn Lys Val Leu
            340                 345                 350

Pro Ile Thr Ile His Gly Asp Ala Ala Val Ile Gly Gln Gly Val Val
            355                 360                 365

Gln Glu Thr Leu Asn Met Ser Gln Ala Arg Gly Tyr Glu Val Gly Gly
        370                 375                 380

Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
                405                 410                 415

Val Leu Ala Pro Ile Phe His Val Asn Ala Asp Asp Pro Glu Ala Val
                420                 425                 430

Ala Phe Val Thr Arg Leu Ala Leu Asp Tyr Arg Asn Thr Phe Lys Arg
            435                 440                 445

Asp Val Phe Ile Asp Leu Val Cys Tyr Arg Arg His Gly His Asn Glu
            450                 455                 460

Ala Asp Glu Pro Ser Ala Thr Gln Pro Leu Met Tyr Gln Lys Ile Lys
465                 470                 475                 480

Lys His Pro Thr Pro Arg Lys Ile Tyr Ala Asp Arg Leu Glu Gly Glu
                485                 490                 495

Gly Val Ala Ser Gln Glu Asp Ala Thr Glu Met Val Asn Leu Tyr Arg
            500                 505                 510

Asp Ala Leu Asp Ala Gly Glu Cys Val Val Pro Glu Trp Arg Pro Met
            515                 520                 525

Ser Leu His Ser Phe Thr Trp Ser Pro Tyr Leu Asn His Glu Trp Asp
        530                 535                 540

Glu Pro Tyr Pro Ala Gln Val Asp Met Lys Arg Leu Lys Glu Leu Ala
545                 550                 555                 560
```

```
Leu Arg Ile Ser Gln Val Pro Glu Gln Ile Glu Val Gln Ser Arg Val
            565                 570                 575
Ala Lys Ile Tyr Asn Asp Arg Lys Leu Met Ala Glu Gly Glu Lys Ala
            580                 585                 590
Phe Asp Trp Gly Gly Ala Glu Asn Leu Ala Tyr Ala Thr Leu Val Asp
            595                 600                 605
Glu Gly Ile Pro Val Arg Leu Ser Gly Glu Asp Ser Gly Arg Gly Thr
    610                 615                 620
Phe Phe His Arg His Ala Val His Asn Gln Ala Asn Gly Ser Thr
625                 630                 635                 640
Tyr Thr Pro Leu His His Ile His Asn Ser Gln Gly Glu Phe Lys Val
            645                 650                 655
Trp Asp Ser Val Leu Ser Glu Glu Ala Val Leu Ala Phe Glu Tyr Gly
            660                 665                 670
Tyr Ala Thr Ala Glu Pro Arg Val Leu Thr Ile Trp Glu Ala Gln Phe
            675                 680                 685
Gly Asp Phe Ala Asn Gly Ala Gln Val Val Ile Asp Gln Phe Ile Ser
            690                 695                 700
Ser Gly Glu Gln Lys Trp Gly Arg Met Cys Gly Leu Val Met Leu Leu
705                 710                 715                 720
Pro His Gly Tyr Glu Gly Gln Gly Pro Glu His Ser Ser Ala Arg Leu
            725                 730                 735
Glu Arg Tyr Leu Gln Leu Cys Ala Glu Gln Asn Met Gln Val Cys Val
            740                 745                 750
Pro Ser Thr Pro Ala Gln Val Tyr His Met Leu Arg Arg Gln Ala Leu
            755                 760                 765
Arg Gly Met Arg Arg Pro Leu Val Val Met Ser Pro Lys Ser Leu Leu
    770                 775                 780
Arg His Pro Leu Ala Ile Ser Ser Leu Asp Glu Leu Ala Asn Gly Ser
785                 790                 795                 800
Phe Gln Pro Ala Ile Gly Glu Ile Asp Asp Leu Asp Pro Gln Gly Val
            805                 810                 815
Lys Arg Val Val Leu Cys Ser Gly Lys Val Tyr Tyr Asp Leu Leu Glu
            820                 825                 830
Gln Arg Arg Lys Asp Glu Lys Thr Asp Val Ala Ile Val Arg Ile Glu
            835                 840                 845
Gln Leu Tyr Pro Phe Pro His Gln Ala Val Gln Glu Ala Leu Lys Ala
    850                 855                 860
Tyr Ser His Val Gln Asp Phe Val Trp Cys Gln Glu Glu Pro Leu Asn
865                 870                 875                 880
Gln Gly Ala Trp Tyr Cys Ser Gln His His Phe Arg Asp Val Val Pro
            885                 890                 895
Phe Gly Ala Thr Leu Arg Tyr Ala Gly Arg Pro Ala Ser Ala Ser Pro
            900                 905                 910
Ala Val Gly Tyr Met Ser Val His Gln Gln Gln Gln Asp Leu Val
            915                 920                 925
Asn Asp Ala Leu Asn Val Asn
    930                 935

<210> SEQ ID NO 4
<211> LENGTH: 407
<212> TYPE: PRT
<213> ORGANISM: Enterobacter agglomerans
```

```
<400> SEQUENCE: 4

Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Ser
            20                  25                  30

Arg Asp Glu Val Ile Val Glu Ile Glu Thr Asp Lys Val Val Leu Glu
        35                  40                  45

Val Pro Ala Ser Ala Asp Gly Val Leu Glu Ala Val Leu Glu Asp Glu
50                  55                  60

Gly Ala Thr Val Thr Ser Arg Gln Ile Leu Gly Arg Leu Lys Glu Gly
65                  70                  75                  80

Asn Ser Ala Gly Lys Glu Ser Ser Ala Lys Ala Glu Ser Asn Asp Thr
                85                  90                  95

Thr Pro Ala Gln Arg Gln Thr Ala Ser Leu Glu Glu Glu Ser Ser Asp
            100                 105                 110

Ala Leu Ser Pro Ala Ile Arg Arg Leu Ile Ala Glu His Asn Leu Asp
        115                 120                 125

Ala Ala Gln Ile Lys Gly Thr Gly Val Gly Gly Arg Leu Thr Arg Glu
    130                 135                 140

Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Ile Asn Met Lys Pro Ile Met Asp Leu Arg Lys Gln Tyr Gly Asp
    210                 215                 220

Ala Phe Glu Lys Arg His Gly Val Arg Leu Gly Phe Met Ser Phe Tyr
225                 230                 235                 240

Ile Lys Ala Val Val Glu Ala Leu Lys Arg Tyr Pro Glu Val Asn Ala
                245                 250                 255

Ser Ile Asp Gly Glu Asp Val Val Tyr His Asn Tyr Phe Asp Val Ser
            260                 265                 270

Ile Ala Val Ser Thr Pro Arg Gly Leu Val Thr Pro Val Leu Arg Asp
        275                 280                 285

Val Asp Ala Leu Ser Met Ala Asp Ile Glu Lys Lys Ile Lys Glu Leu
    290                 295                 300

Ala Val Lys Gly Arg Asp Gly Lys Leu Thr Val Asp Asp Leu Thr Gly
305                 310                 315                 320

Gly Asn Phe Thr Ile Thr Asn Gly Gly Val Phe Gly Ser Leu Met Ser
                325                 330                 335

Thr Pro Ile Ile Asn Pro Pro Gln Ser Ala Ile Leu Gly Met His Ala
            340                 345                 350

Ile Lys Asp Arg Pro Met Ala Val Asn Gly Gln Val Val Ile Leu Pro
        355                 360                 365

Met Met Tyr Leu Ala Leu Ser Tyr Asp His Arg Leu Ile Asp Gly Arg
    370                 375                 380

Glu Ser Val Gly Tyr Leu Val Ala Val Lys Glu Met Leu Glu Asp Pro
385                 390                 395                 400

Ala Arg Leu Leu Leu Asp Val
                405
```

<210> SEQ ID NO 5
<211> LENGTH: 40
<212> TYPE: PRT
<213> ORGANISM: Enterobacter agglomerans

<400> SEQUENCE: 5

Met Asn Leu His Glu Tyr Gln Ala Lys Gln Leu Phe Ala Arg Tyr Gly
1               5                   10                  15

Met Pro Ala Pro Thr Gly Tyr Ala Cys Thr Thr Pro Arg Glu Ala Glu
            20                  25                  30

Glu Ala Ala Ser Lys Ile Gly Ala
        35                  40

<210> SEQ ID NO 6
<211> LENGTH: 30
<212> TYPE: DNA
<213> ORGANISM: Artificial Sequence
<220> FEATURE:
<223> OTHER INFORMATION: synthetic DNA

<400> SEQUENCE: 6
gtcgacaata gccygaatct gttctggtcg                                          30

<210> SEQ ID NO 7
<211> LENGTH: 30
<212> TYPE: DNA
<213> ORGANISM: Artificial Sequence
<220> FEATURE:
<223> OTHER INFORMATION: synthetic DNA

<400> SEQUENCE: 7
aagcttatcg acgctccoct ccccaccgtt                                          30

<210> SEQ ID NO 8
<211> LENGTH: 935
<212> TYPE: PRT
<213> ORGANISM: Enterobacter agglomerans

<400> SEQUENCE: 8

Met Gln Asn Ser Ala Met Lys Pro Trp Leu Asp Ser Ser Trp Leu Ala
1               5                   10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45

Pro Gly Thr Gly Val Lys Pro Glu Gln Phe His Ser Ala Thr Arg Glu
    50                  55                  60

Tyr Phe Arg Arg Leu Ala Lys Asp Ala Ser Arg Tyr Thr Ser Ser Val
65                  70                  75                  80

Thr Asp Pro Ala Thr Asn Ser Lys Gln Val Lys Val Leu Gln Leu Ile
                85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

Asp Leu Thr Asp Ala Asp Phe Gln Glu Ser Phe Asn Val Gly Ser Phe
    130                 135                 140

Ala Ile Gly Lys Glu Thr Met Lys Leu Ala Asp Leu Phe Asp Ala Leu
145                 150                 155                 160

```
Lys Gln Thr Tyr Cys Gly Ser Ile Gly Ala Glu Tyr Met His Ile Asn
                165                 170                 175
Asn Thr Glu Glu Lys Arg Trp Ile Gln Gln Arg Ile Glu Ser Gly Ala
            180                 185                 190
Ser Gln Thr Ser Phe Ser Gly Glu Glu Lys Lys Gly Phe Leu Lys Glu
        195                 200                 205
Leu Thr Ala Ala Glu Gly Leu Glu Lys Tyr Leu Gly Ala Lys Phe Pro
    210                 215                 220
Gly Ala Lys Arg Phe Ser Leu Gly Gly Asp Ala Leu Val Pro Met
225                 230                 235                 240
Leu Arg Glu Met Ile Arg His Ala Gly Lys Ser Gly Thr Arg Glu Val
                245                 250                 255
Val Leu Gly Met Ala His Arg Gly Arg Leu Asn Val Leu Ile Asn Val
                260                 265                 270
Leu Gly Lys Lys Pro Gln Asp Leu Phe Asp Glu Phe Ser Gly Lys His
                275                 280                 285
Lys Glu His Leu Gly Thr Gly Asp Val Lys Tyr His Met Gly Phe Ser
            290                 295                 300
Ser Asp Ile Glu Thr Glu Gly Gly Leu Val His Leu Ala Leu Ala Phe
305                 310                 315                 320
Asn Pro Ser His Leu Glu Ile Val Ser Pro Val Val Met Gly Ser Val
                325                 330                 335
Arg Ala Arg Leu Asp Arg Leu Ala Glu Pro Val Ser Asn Lys Val Leu
                340                 345                 350
Pro Ile Thr Ile His Gly Asp Ala Ala Val Ile Gly Gln Gly Val Val
                355                 360                 365
Gln Glu Thr Leu Asn Met Ser Gln Ala Arg Gly Tyr Glu Val Gly Gly
            370                 375                 380
Thr Val Arg Ile Val Ile Asn Asn Gln Val Gly Phe Thr Thr Ser Asn
385                 390                 395                 400
Pro Lys Asp Ala Arg Ser Thr Pro Tyr Cys Thr Asp Ile Gly Lys Met
                405                 410                 415
Val Leu Ala Pro Ile Phe His Val Asn Ala Asp Asp Pro Glu Ala Val
                420                 425                 430
Ala Phe Val Thr Arg Leu Ala Leu Asp Tyr Arg Asn Thr Phe Lys Arg
            435                 440                 445
Asp Val Phe Ile Asp Leu Val Cys Tyr Arg Arg His Gly His Asn Glu
        450                 455                 460
Ala Asp Glu Pro Ser Ala Thr Gln Pro Leu Met Tyr Gln Lys Ile Lys
465                 470                 475                 480
Lys His Pro Thr Pro Arg Lys Ile Tyr Ala Asp Arg Leu Glu Gly Glu
                485                 490                 495
Gly Val Ala Ser Gln Glu Asp Ala Thr Glu Met Val Asn Leu Tyr Arg
            500                 505                 510
Asp Ala Leu Asp Ala Gly Glu Cys Val Val Pro Glu Trp Arg Pro Met
        515                 520                 525
Ser Leu His Ser Phe Thr Trp Ser Pro Tyr Leu Asn His Glu Trp Asp
    530                 535                 540
Glu Pro Tyr Pro Ala Gln Val Asp Met Lys Arg Leu Lys Glu Leu Ala
545                 550                 555                 560
Leu Arg Ile Ser Gln Val Pro Glu Gln Ile Glu Val Gln Ser Arg Val
                565                 570                 575
```

-continued

```
Ala Lys Ile Tyr Asn Asp Arg Lys Leu Met Ala Glu Gly Glu Lys Ala
            580                 585                 590

Phe Asp Trp Gly Gly Ala Glu Asn Leu Ala Tyr Ala Thr Leu Val Asp
        595                 600                 605

Glu Gly Ile Pro Val Arg Leu Ser Gly Glu Asp Ser Gly Arg Gly Thr
    610                 615                 620

Phe Phe His Arg His Ala Val Val His Asn Gln Ala Asn Gly Ser Thr
625                 630                 635                 640

Tyr Thr Pro Leu His His Ile His Asn Ser Gln Gly Glu Phe Lys Val
                645                 650                 655

Trp Asp Ser Val Leu Ser Glu Glu Ala Val Leu Ala Phe Glu Tyr Gly
            660                 665                 670

Tyr Ala Thr Ala Glu Pro Arg Val Leu Thr Ile Trp Glu Ala Gln Phe
        675                 680                 685

Gly Asp Phe Ala Asn Gly Ala Gln Val Val Ile Asp Gln Phe Ile Ser
    690                 695                 700

Ser Gly Glu Gln Lys Trp Gly Arg Met Cys Gly Leu Val Met Leu Leu
705                 710                 715                 720

Pro His Gly Tyr Glu Gly Gln Gly Pro Glu His Ser Ser Ala Arg Leu
                725                 730                 735

Glu Arg Tyr Leu Gln Leu Cys Ala Glu Gln Asn Met Gln Val Cys Val
            740                 745                 750

Pro Ser Thr Pro Ala Gln Val Tyr His Met Leu Arg Arg Gln Ala Leu
        755                 760                 765

Arg Gly Met Arg Arg Pro Leu Val Val Met Ser Pro Lys Ser Leu Leu
    770                 775                 780

Arg His Pro Leu Ala Ile Ser Ser Leu Asp Glu Leu Ala Asn Gly Ser
785                 790                 795                 800

Phe Gln Pro Ala Ile Gly Glu Ile Asp Asp Leu Asp Pro Gln Gly Val
                805                 810                 815

Lys Arg Val Val Leu Cys Ser Gly Lys Val Tyr Tyr Asp Leu Leu Glu
            820                 825                 830

Gln Arg Arg Lys Asp Glu Lys Thr Asp Val Ala Ile Val Arg Ile Glu
        835                 840                 845

Gln Leu Tyr Pro Phe Pro His Gln Ala Val Gln Glu Ala Leu Lys Ala
    850                 855                 860

Tyr Ser His Val Gln Asp Phe Val Trp Cys Gln Glu Glu Pro Leu Asn
865                 870                 875                 880

Gln Gly Ala Trp Tyr Cys Ser Gln His His Phe Arg Asp Val Val Pro
                885                 890                 895

Phe Gly Ala Thr Leu Arg Tyr Ala Gly Arg Pro Ala Ser Ala Ser Pro
            900                 905                 910

Ala Val Gly Tyr Met Ser Val His Gln Gln Gln Gln Asp Leu Val
        915                 920                 925

Asn Asp Ala Leu Asn Val Asn
    930                 935
```

<210> SEQ ID NO 9
<211> LENGTH: 933
<212> TYPE: PRT
<213> ORGANISM: Escherichia coli

<400> SEQUENCE: 9

```
Met Gln Asn Ser Ala Leu Lys Ala Trp Leu Asp Ser Ser Tyr Leu Ser
1               5                   10                  15
```

```
Gly Ala Asn Gln Ser Trp Ile Glu Gln Leu Tyr Glu Asp Phe Leu Thr
            20                  25                  30

Asp Pro Asp Ser Val Asp Ala Asn Trp Arg Ser Thr Phe Gln Gln Leu
        35                  40                  45

Pro Gly Thr Gly Val Lys Pro Asp Gln Phe His Ser Gln Thr Arg Glu
    50                  55                  60

Tyr Phe Arg Arg Leu Ala Lys Asp Ala Ser Arg Tyr Ser Ser Thr Ile
65                  70                  75                  80

Ser Asp Pro Asp Thr Asn Val Lys Gln Val Lys Val Leu Gln Leu Ile
                85                  90                  95

Asn Ala Tyr Arg Phe Arg Gly His Gln His Ala Asn Leu Asp Pro Leu
            100                 105                 110

Gly Leu Trp Gln Gln Asp Lys Val Ala Asp Leu Asp Pro Ser Phe His
        115                 120                 125

Asp Leu Thr Glu Ala Asp Phe Gln Glu Thr Phe Asn Val Gly Ser Phe
    130                 135                 140

Ala Ser Gly Lys Glu Thr Met Lys Leu Gly Glu Leu Leu Glu Ala Leu
145                 150                 155                 160

Lys Gln Thr Tyr Cys Gly Pro Ile Gly Ala Glu Tyr Met His Ile Thr
                165                 170                 175

Ser Thr Glu Glu Lys Arg Trp Ile Gln Gln Arg Ile Glu Ser Gly Arg
            180                 185                 190

Ala Thr Phe Asn Ser Glu Glu Lys Lys Arg Phe Leu Ser Glu Leu Thr
        195                 200                 205

Ala Ala Glu Gly Leu Glu Arg Tyr Leu Gly Ala Lys Phe Pro Gly Ala
    210                 215                 220

Lys Arg Phe Ser Leu Glu Gly Asp Ala Leu Ile Pro Met Leu Lys
225                 230                 235                 240

Glu Met Ile Arg His Ala Gly Asn Ser Gly Thr Arg Glu Val Val Leu
                245                 250                 255

Gly Met Ala His Arg Gly Arg Leu Asn Val Leu Val Asn Val Leu Gly
            260                 265                 270

Lys Lys Pro Gln Asp Leu Phe Asp Glu Phe Ala Gly Lys His Lys Glu
        275                 280                 285

His Leu Gly Thr Gly Asp Val Lys Tyr His Met Gly Phe Ser Ser Asp
    290                 295                 300

Phe Gln Thr Asp Gly Gly Leu Val His Leu Ala Leu Ala Phe Asn Pro
305                 310                 315                 320

Ser His Leu Glu Ile Val Ser Pro Val Val Ile Gly Ser Val Arg Ala
                325                 330                 335

Arg Leu Asp Arg Leu Asp Glu Pro Ser Ser Asn Lys Val Leu Pro Ile
            340                 345                 350

Thr Ile His Gly Asp Ala Ala Val Thr Gly Gln Gly Val Val Gln Glu
        355                 360                 365

Thr Leu Asn Met Ser Lys Ala Arg Gly Tyr Glu Val Gly Gly Thr Val
    370                 375                 380

Arg Ile Val Ile Asn Asn Gln Val Gly Phe Thr Thr Ser Asn Pro Leu
385                 390                 395                 400

Asp Ala Arg Ser Thr Pro Tyr Cys Thr Asp Ile Gly Lys Met Val Gln
                405                 410                 415

Ala Pro Ile Phe His Val Asn Ala Asp Asp Pro Glu Ala Val Ala Phe
            420                 425                 430
```

```
Val Thr Arg Leu Ala Leu Asp Phe Arg Asn Thr Phe Lys Arg Asp Val
        435                 440                 445

Phe Ile Asp Leu Val Ser Tyr Arg Arg His Gly His Asn Glu Ala Asp
    450                 455                 460

Glu Pro Ser Ala Thr Gln Pro Leu Met Tyr Gln Lys Ile Lys Lys His
465                 470                  475                 480

Pro Thr Pro Arg Lys Ile Tyr Ala Asp Lys Leu Glu Gln Glu Lys Val
            485                 490                 495

Ala Thr Leu Glu Asp Ala Thr Glu Met Val Asn Leu Tyr Arg Asp Ala
                500                 505                 510

Leu Asp Ala Gly Asp Cys Val Val Ala Glu Trp Arg Pro Met Asn Met
            515                 520                 525

His Ser Phe Thr Trp Ser Pro Tyr Leu Asn His Glu Trp Asp Glu Glu
    530                 535                 540

Tyr Pro Asn Lys Val Glu Met Lys Arg Leu Gln Glu Leu Ala Lys Arg
545                 550                 555                 560

Ile Ser Thr Val Pro Glu Ala Val Glu Met Gln Ser Arg Val Ala Lys
                565                 570                 575

Ile Tyr Gly Asp Arg Gln Ala Met Ala Ala Gly Glu Lys Leu Phe Asp
            580                 585                 590

Trp Gly Gly Ala Glu Asn Leu Ala Tyr Ala Thr Leu Val Asp Glu Gly
    595                 600                 605

Ile Pro Val Arg Leu Ser Gly Glu Asp Ser Gly Arg Gly Thr Phe Phe
            610                 615                 620

His Arg His Ala Val Ile His Asn Gln Ser Asn Gly Ser Thr Tyr Thr
625                 630                 635                 640

Pro Leu Gln His Ile His Asn Gly Gln Gly Ala Phe Arg Val Trp Asp
                645                 650                 655

Ser Val Leu Ser Glu Glu Ala Val Leu Ala Phe Glu Tyr Gly Tyr Ala
            660                 665                 670

Thr Ala Glu Pro Arg Thr Leu Thr Ile Trp Glu Ala Gln Phe Gly Asp
    675                 680                 685

Phe Ala Asn Gly Ala Gln Val Val Ile Asp Gln Phe Ile Ser Ser Gly
    690                 695                 700

Glu Gln Lys Trp Gly Arg Met Cys Gly Leu Val Met Leu Leu Pro His
705                 710                 715                 720

Gly Tyr Glu Gly Gln Gly Pro Glu His Ser Ser Ala Arg Leu Glu Arg
                725                 730                 735

Tyr Leu Gln Leu Cys Ala Glu Gln Asn Met Gln Val Cys Val Pro Ser
            740                 745                 750

Thr Pro Ala Gln Val Tyr His Met Leu Arg Arg Gln Ala Leu Arg Gly
    755                 760                 765

Met Arg Arg Pro Leu Val Val Met Ser Pro Lys Ser Leu Leu Arg His
    770                 775                 780

Pro Leu Ala Val Ser Ser Leu Glu Glu Leu Ala Asn Gly Thr Phe Leu
785                 790                 795                 800

Pro Ala Ile Gly Glu Ile Asp Glu Leu Asp Pro Lys Gly Val Lys Arg
                805                 810                 815

Val Val Met Cys Ser Gly Lys Val Tyr Tyr Asp Leu Leu Glu Gln Arg
            820                 825                 830

Arg Lys Asn Asn Gln His Asp Val Ala Ile Val Arg Ile Glu Gln Leu
    835                 840                 845

Tyr Pro Phe Pro His Lys Ala Met Gln Glu Val Leu Gln Gln Phe Ala
```

```
                850              855              860
His Val Lys Asp Phe Val Trp Cys Gln Glu Glu Pro Leu Asn Gln Gly
865              870              875              880

Ala Trp Tyr Cys Ser Gln His His Phe Arg Glu Val Ile Pro Phe Gly
                885              890              895

Ala Ser Leu Arg Tyr Ala Gly Arg Pro Ala Ser Ala Ser Pro Ala Val
                900              905              910

Gly Tyr Met Ser Val His Gln Lys Gln Gln Gln Asp Leu Val Asn Asp
            915              920              925

Ala Leu Asn Val Glu
        930

<210> SEQ ID NO 10
<211> LENGTH: 407
<212> TYPE: PRT
<213> ORGANISM: Enterobacter agglomerans

<400> SEQUENCE: 10

Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Ser
                20                  25                  30

Arg Asp Glu Val Ile Val Glu Ile Glu Thr Asp Lys Val Val Leu Glu
            35                  40                  45

Val Pro Ala Ser Ala Asp Gly Val Leu Glu Ala Val Leu Glu Asp Glu
        50                  55                  60

Gly Ala Thr Val Thr Ser Arg Gln Ile Leu Gly Arg Leu Lys Glu Gly
65                  70                  75                  80

Asn Ser Ala Gly Lys Glu Ser Ser Ala Lys Ala Glu Ser Asn Asp Thr
                85                  90                  95

Thr Pro Ala Gln Arg Gln Thr Ala Ser Leu Glu Glu Ser Ser Asp
                100             105                 110

Ala Leu Ser Pro Ala Ile Arg Arg Leu Ile Ala Glu His Asn Leu Asp
            115                 120                 125

Ala Ala Gln Ile Lys Gly Thr Gly Val Gly Gly Arg Leu Thr Arg Glu
130                 135                 140

Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Ile Asn Met Lys Pro Ile Met Asp Leu Arg Lys Gln Tyr Gly Asp
        210                 215                 220

Ala Phe Glu Lys Arg His Gly Val Arg Leu Gly Phe Met Ser Phe Tyr
225                 230                 235                 240

Ile Lys Ala Val Val Glu Ala Leu Lys Arg Tyr Pro Glu Val Asn Ala
                245                 250                 255

Ser Ile Asp Gly Glu Asp Val Val Tyr His Asn Tyr Phe Asp Val Ser
            260                 265                 270

Ile Ala Val Ser Thr Pro Arg Gly Leu Val Thr Pro Val Leu Arg Asp
        275                 280                 285
```

```
Val Asp Ala Leu Ser Met Ala Asp Ile Glu Lys Lys Ile Lys Glu Leu
        290                 295                 300

Ala Val Lys Gly Arg Asp Gly Lys Leu Thr Val Asp Leu Thr Gly
305                 310                 315                 320

Gly Asn Phe Thr Ile Thr Asn Gly Gly Val Phe Gly Ser Leu Met Ser
                325                 330                 335

Thr Pro Ile Ile Asn Pro Pro Gln Ser Ala Ile Leu Gly Met His Ala
                340                 345                 350

Ile Lys Asp Arg Pro Met Ala Val Asn Gly Gln Val Val Ile Leu Pro
                355                 360                 365

Met Met Tyr Leu Ala Leu Ser Tyr Asp His Arg Leu Ile Asp Gly Arg
        370                 375                 380

Glu Ser Val Gly Tyr Leu Val Ala Val Lys Glu Met Leu Glu Asp Pro
385                 390                 395                 400

Ala Arg Leu Leu Leu Asp Val
                405

<210> SEQ ID NO 11
<211> LENGTH: 407
<212> TYPE: PRT
<213> ORGANISM: Escherichia coli

<400> SEQUENCE: 11

Met Ser Ser Val Asp Ile Leu Val Pro Asp Leu Pro Glu Ser Val Ala
1               5                   10                  15

Asp Ala Thr Val Ala Thr Trp His Lys Lys Pro Gly Asp Ala Val Val
                20                  25                  30

Arg Asp Glu Val Leu Val Glu Ile Glu Thr Asp Lys Val Val Leu Glu
            35                  40                  45

Val Pro Ala Ser Ala Asp Gly Ile Leu Asp Ala Val Leu Glu Asp Glu
        50                  55                  60

Gly Thr Thr Val Thr Ser Arg Gln Ile Leu Gly Arg Leu Arg Glu Gly
65                  70                  75                  80

Asn Ser Ala Gly Lys Glu Thr Ser Ala Lys Ser Glu Glu Lys Ala Ser
                85                  90                  95

Thr Pro Ala Gln Arg Gln Gln Ala Ser Leu Glu Glu Gln Asn Asn Asp
                100                 105                 110

Ala Leu Ser Pro Ala Ile Arg Arg Leu Ile Ala Glu His Asn Leu Asp
            115                 120                 125

Ala Ala Gln Ile Lys Gly Thr Gly Val Gly Gly Arg Leu Thr Arg Glu
        130                 135                 140

Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Val Asn Met Lys Pro Ile Met Asp Leu Arg Lys Gln Tyr Gly Glu
210                 215                 220

Ala Phe Glu Lys Arg His Gly Ile Arg Leu Gly Phe Met Ser Phe Tyr
225                 230                 235                 240

Val Lys Ala Val Val Glu Ala Leu Lys Arg Tyr Pro Glu Val Asn Ala
                245                 250                 255
```

-continued

```
Ser Ile Asp Gly Asp Asp Val Val Tyr His Asn Tyr Phe Asp Val Ser
            260                 265                 270

Met Ala Val Ser Thr Pro Arg Gly Leu Val Thr Pro Val Leu Arg Asp
            275                 280                 285

Val Asp Thr Leu Gly Met Ala Asp Ile Glu Lys Lys Ile Lys Glu Leu
            290                 295                 300

Ala Val Lys Gly Arg Asp Gly Lys Leu Thr Val Glu Asp Leu Thr Gly
305                 310                 315                 320

Gly Asn Phe Thr Ile Thr Asn Gly Gly Val Phe Gly Ser Leu Met Ser
                    325                 330                 335

Thr Pro Ile Ile Asn Pro Pro Gln Ser Ala Ile Leu Gly Met His Ala
            340                 345                 350

Ile Lys Asp Arg Pro Met Ala Val Asn Gly Gln Val Glu Ile Leu Pro
            355                 360                 365

Met Met Tyr Leu Ala Leu Ser Tyr Asp His Arg Leu Ile Asp Gly Arg
    370                 375                 380

Glu Ser Val Gly Phe Leu Val Thr Ile Lys Glu Leu Leu Glu Asp Pro
385                 390                 395                 400

Thr Arg Leu Leu Leu Asp Val
                405

<210> SEQ ID NO 12
<211> LENGTH: 41
<212> TYPE: PRT
<213> ORGANISM: Enterobacter agglomerans

<400> SEQUENCE: 12

Met Asn Leu His Glu Tyr Gly Ala Lys Gln Leu Phe Ala Arg Tyr Gly
1               5                   10                  15

Met Pro Ala Pro Thr Gly Tyr Ala Cys Thr Thr Pro Arg Glu Ala Glu
            20                  25                  30

Glu Ala Ala Ser Lys Ile Gly Ala Gly
        35                  40

<210> SEQ ID NO 13
<211> LENGTH: 60
<212> TYPE: PRT
<213> ORGANISM: Escherichia coli

<400> SEQUENCE: 13

Met Asn Leu His Glu Tyr Gln Ala Lys Gln Leu Phe Ala Arg Tyr Gly
1               5                   10                  15

Leu Pro Ala Pro Val Gly Tyr Ala Cys Thr Thr Pro Arg Glu Ala Glu
            20                  25                  30

Glu Ala Ala Ser Lys Ile Gly Ala Gly Pro Trp Val Val Lys Cys Gln
        35                  40                  45

Val His Ala Gly Gly Arg Gly Lys Ala Gly Gly Val
    50                  55                  60

<210> SEQ ID NO 14
<211> LENGTH: 39
<212> TYPE: PRT
<213> ORGANISM: Enterobacter agglomerans

<400> SEQUENCE: 14

Ala Phe Ser Val Phe Arg Cys His Ser Ile Met Asn Cys Val Ser Val
1               5                   10                  15
```

-continued

```
Cys Pro Lys Gly Leu Asn Pro Thr Arg Ala Ile Gly His Ile Lys Ser
            20                  25                  30

Met Leu Leu Gln Arg Ser Ala
            35

<210> SEQ ID NO 15
<211> LENGTH: 58
<212> TYPE: PRT
<213> ORGANISM: Escherichia coli

<400> SEQUENCE: 15

Phe Leu Ile Asp Ser Arg Asp Thr Glu Thr Asp Ser Arg Leu Asp Gly
1               5                   10                  15

Leu Ser Asp Ala Phe Ser Val Phe Arg Cys His Ser Ile Met Asn Cys
            20                  25                  30

Val Ser Val Cys Pro Lys Gly Leu Asn Pro Thr Arg Ala Ile Gly His
            35                  40                  45

Ile Lys Ser Met Leu Leu Gln Arg Asn Ala
    50                  55
```